(12) United States Patent
Kaczka et al.

(10) Patent No.: US 10,675,423 B2
(45) Date of Patent: Jun. 9, 2020

(54) SYSTEMS AND METHODS FOR MULTI-FREQUENCY OSCILLATORY VENTILATION

(71) Applicants: David Kaczka, Iowa City, IA (US); Jacob Herrmann, Coralville, IA (US)

(72) Inventors: David Kaczka, Iowa City, IA (US); Jacob Herrmann, Coralville, IA (US)

(*) Notice: Subject to any disclaimer, the term of this patent is extended or adjusted under 35 U.S.C. 154(b) by 1072 days.

(21) Appl. No.: 15/145,880

(22) Filed: May 4, 2016

(65) Prior Publication Data

US 2016/0339191 A1    Nov. 24, 2016

Related U.S. Application Data

(60) Provisional application No. 62/163,737, filed on May 19, 2015.

(51) Int. Cl.
*A61M 16/00* (2006.01)
*A61M 16/20* (2006.01)
*A61M 16/10* (2006.01)

(52) U.S. Cl.
CPC .... *A61M 16/0057* (2013.01); *A61M 16/0006* (2014.02); *A61M 16/0096* (2013.01); *A61M 16/203* (2014.02); *A61M 2016/0027* (2013.01); *A61M 2016/0036* (2013.01); *A61M 2016/102* (2013.01); *A61M 2230/005* (2013.01); *A61M 2230/202* (2013.01); *A61M 2230/205* (2013.01); *A61M 2230/208* (2013.01); *A61M 2230/40* (2013.01); *A61M 2230/46* (2013.01)

(58) Field of Classification Search
CPC .......... A61M 16/0006; A61M 16/0057; A61M 16/0096; A61M 16/203
See application file for complete search history.

(56) References Cited

U.S. PATENT DOCUMENTS

| 4,747,403 A | 5/1988 | Gluck et al. |
| 4,821,709 A | 4/1989 | Jensen |
| 6,112,744 A | 9/2000 | Hognelid |

(Continued)

FOREIGN PATENT DOCUMENTS

| WO | WO2013163740 A1 | 11/2013 |
| WO | 2014111828 A1 | 7/2014 |

(Continued)

OTHER PUBLICATIONS

Fessler, et al., A protocol for high-frequency oscillatory ventilation in adults: Results from a roundtable discussion, Critical Care Medicine, vol. 35, No. 7, Society for Critical Care Medicine and Lippincott Williams & Wilkins, 2007.

(Continued)

*Primary Examiner* — Valerie L Woodward
(74) *Attorney, Agent, or Firm* — Shuttleworth & Ingersoll, PLC; Jason Sytsma

(57) ABSTRACT

Oscillatory ventilator configured for oscillating at a plurality of specifically tuned sinusoidal frequencies simultaneously a ventilation gas for delivery to a lung region of a patient and a ventilator control system, in communication with the oscillatory ventilator, to control a sinusoidal waveform input for the oscillatory ventilator, wherein the sinusoidal waveform input comprises the plurality of specifically tuned sinusoidal frequencies each of which sinusoidal frequencies are below the acoustic range.

20 Claims, 16 Drawing Sheets

(56) References Cited

U.S. PATENT DOCUMENTS

| | | | |
|---|---|---|---|
| 7,770,580 B2* | 8/2010 | Kruger | A61M 16/0096 128/204.18 |
| 8,402,970 B2 | 3/2013 | Levi et al. | |
| 2001/0003984 A1* | 6/2001 | Bennarsten | A61M 16/0096 128/204.21 |
| 2004/0069304 A1* | 4/2004 | Jam | A61M 16/021 128/204.18 |
| 2007/0006924 A1* | 1/2007 | Kaczka | A61M 16/0096 137/458 |
| 2009/0007913 A1 | 1/2009 | Lee | |
| 2013/0220324 A1 | 8/2013 | Jafari et al. | |
| 2014/0190481 A1* | 7/2014 | Jam | A61M 16/0006 128/203.12 |
| 2014/0251329 A1 | 9/2014 | Bostick | |
| 2018/0104426 A1* | 4/2018 | Oldfield | A61M 16/0096 |

FOREIGN PATENT DOCUMENTS

| | | | |
|---|---|---|---|
| WO | WO-2014111828 A1 * | 7/2014 | A61M 16/0069 |
| WO | WO2014120842 A1 | 8/2014 | |
| WO | WO2015021350 A1 | 2/2015 | |

OTHER PUBLICATIONS

Fessler, et al., Feasibility of very high-frequency ventilation in adults with acute respiratory distress syndrome, Critical Care Medicine, vol. 36, No. 4, Society of Critical Care Medicine and Lippincott Williams & Wilkins, 2008.

Fortune, et al., Effects of common dead space on inert gas exchange in mathematical models of the lung, the American Physiological Society, 1979.

Fredberg, Jeffrey A., Augmented diffusion in the airways can support pulmonary gas exchange, the American Physiological Society, 1980.

Fredberg, et al., Alveolar pressure nonhomogeneity during small-amplitude high-frequency oscillation, the American Physiological Society, 1984.

Fredberg, et al., Factors influencing mechanical performance of neonatal high-frequency ventilators, the American Physiological Society, 1987.

Fredberg, Inez, Electrical impedance tomography (EIT) in applications related to lung and ventilation: a review of experimental and clinical activities, Physiological Measurement 21, IOP Publishing Ltd., 2000.

Fredberg, et al., Lung Volume Recruitment after Surfactant Administration Modifies Spatial Distribution of Ventilation, American Journal of Respiratory Critical Care Medicine, vol. 174, Jul. 13, 2006.

Frerichs, et al., Monitoring perioperative changes in distribution of pulmonary ventilation by functional electrical impedance tomography, Acta Anaesthesiological Scandinavica, 1998.

Fuld, et al., CT-measured regional specific volume change reflects regional ventilation in supine sheep, Journal of Applied Physiology 104: 1177-1184, the American Physiological Society, 2008.

Fuld, et al., Optimization of Dual-Energy Xenon-Computed Tomography for Quantitative Assessment of Regional Pulmonary Ventilation, Investigative Radiology, vol. 48, No. 9, Sep. 2013, Lippincott Williams & Wilkins.

Gattinoni, et al., Lung Recruitment in Patients with the Acute Respiratory Distress Syndrome, The New England Journal of Medicine, vol. 354, No. 17, Apr. 27, 2006, Massachusetts Medical Society, 2006.

Gerstmann, et al., The Provo Multicenter Early High-Frequency Oscillatory Ventilation Trial: Improved Pulmonary and Clinical Outcome in Respiratory Distress Syndrome, Pediatrics, vol. 98, No. 6, Dec. 1996, American Academy of Pediatrics 1996.

Goffi, et al., High-frequency oscillatory ventilation for early acute respiratory distress syndrome in adults, Current Opinion Critical Care 2014, 20:77-85, Wolters Kluwer Health/Lippincott Williams & Wilkins 2014.

Goligher, et al., Re-evaluating high-frequency oscillation for ARDS: Would a targeted approach be successful? Critical Care 2013, 17:133, Biomed Central Ltd. 2013.

Hacking, et al., Respiratory distress syndrome and birth order in premature twins, Archives of Disease in Childhood—Fetal Neonatal Ed 2001; 84:F117-F121.

Hager, et al., Four methods of measuring tidal volume during high-frequency oscillatory ventilation, Critical Care Medicine, vol. 34, No. 3, Society of Critical Care Medicine and Lippincott Williams & Wilkins, 2006.

Hager, et al., Tidal volume delivery during high-frequency oscillatory ventilation in adults with acute respiratory distress syndrome, Critical Care Medicine, vol. 35, No. 6, Society of Critical Care Medicine and Lippincott Williams & Wilkins, 2007.

Hager, David N., High-frequency oscillatory ventilation in adults with acute respiratory distress syndrome, Current Opinion Anesthesiology 2012, 25:17-23, Wolters Kluwer Health/Lippincott Williams & Wilkins, 2012.

Harcourt, et al., Pressure and Flow Waveform Characteristics of Eight High-Frequency Oscillators, Pediatric Critical Care Medicine, Society of Critical Care Medicine and the World Federation of Pediatric Intensive and Critical Care Societies, 2014.

Harf, et al., Mechanical Ventilation With Superimposed High Frequency Oscillation in the Normal Rat, Respiratory Physiology (1983) 54, 31-40, Elxevier Science Publishers B.V., 1983.

Haskins, et al., Reference Cardiopulmonary Values in Normal Dogs, Comparative Medicine, vol. 55, No. 2, Apr. 2005, The American Association for Laboratory Animal Science.

Henderson, et al., Airway pressure and transpulmonary pressure during high-frequency oscillation for acute respiratory distress syndrome, Canadian Respiratory Journal 2014; 21 (2): 107-111, Pulsus Group, Inc. 2014.

Herridge, Margaret S., Recovery and Long-Term Outcome in Acute Respiratory Distress Syndrome, Critical Care Clinics 27 (2011) 685-704, Elsevier, Inc. 2011.

Herridge, et al., Functional Disability 5 Years after Acute Respiratory Distress Syndrome, The New England Journal of Medicine, vol. 364, No. 14, Apr. 7, 2011, Massachusetts Medical Society, 2011.

Hoag, et al., Recirculation of Inhaled Xenon Does Not alter Lung CT Density, Laboratory Investigations, Academy of Radiology 2007; 14:81-84.

Hoegger, et al., Assessing mucociliary transport of single particles in vivo shows variable speed and preference for the ventral trachea in newborn pigs, PNAS, Feb. 11, 2014, vol. 111, No. 6, 2355-2360, Proceedings of the National Academy of Sciences 2014.

Hough, et al., Long-term outcome after acute lung injury, Current Opinion Review, vol. 18, No. 1, Feb. 2012, Current Opinion Critical Care 2012.

Hu, et al., Automatic Lung Segmentation for Acute Quantitation of Volumetric X-Ray CT Images, IEEE Transactions on Medical Imaging, vol. 20, No. 6, Jun. 2001, IEEE 2001.

Hurst, et al., Comparison of Conventional Mechanical Ventilation and High-frequency Ventilation A Prospective, Randomized Trial in Patient with Respiratory Failure, Ann. Surg., Apr. 1990, vol. 211, No. 4.

Jahani, et al., Assessment of regional non-linear tissue deformation and air volume change of human lungs via image registration, Journal of Biomechanics 47 (2014) 1626-1633, Elsevier Ltd., 2014.

Jobe, et al., Mechanisms initiating lung injury in the preterm, Early Human Development 53 (1998) 81-94, Elsevier Science Ireland Ltd., 1998.

John, et al., Drager VN500's oscillatory performance has a frequency-dependent threshold, Journal of Paediatrics and Child Health 50 (2014) 27-31.

Kaczka, et al., Servo-Controlled Pneumatic Pressure Oscillatory for Respiratory Impedance Measurements and High-Frequency Ventilation, Annals of Biomedical Engineering, vol. 32, No. 4, Apr. 2004, pp. 596-608, Biomedical Engineering Society, 2004.

Kaczka, et al., Quantifying Mechanical Heterogeneity in Canine Acute Lung Injury, Anesthesiology 2005, 103:306-17, American Society of Anesthesiologists, Inc. Lippincott Williams & Wilkins, Inc. 2005.

(56) References Cited

OTHER PUBLICATIONS

Kaczka, et al., Reliability of Estimating Stochastic Lung Tissue Heterogeneity from Pulmonary Impedance Spectra: A Forward-Inverse Modeling Study, Annals of Biomedical Engineering, vol. 35, No. 10, Oct. 2007, pp. 1722-1738, Biomedical Engineering Society, 2007.
Kaczka, et al., Assessment of Heterogeneous airway constriction in dogs: a structure-function analysis, Journal of Applied Physiology 106: 520-530, 2009, The American Physiological Society, 2009.
Kaczka, et al., Analysis of Regional Mechanics in Canine Lung Injury Using Forced Oscillations and 3D Image Registration, Annals of Biomedical Engineering, vol. 39, No. 3, Mar. 2011, pp. 1112-1124.
Kaczka, et al., Chapter 10 Computational Analysis of Airway Flow and Lung Tissue Dynamics, Springer Science+Business media, LLC 2011.
Kaczka, et al., Oscillation Mechanics of the Respiratory System: Applications to Lung Disease, Critical Reviews in Biomedical Engineering, 39(4):337-359 (2011), Begell House, Inc. 2011.
Kaczka, et al., Constant-phase descriptions of canine, lung, chest wall, and total respiratory system viscoelasticity: Effects of distending pressure, Respiratory Physiology & Neurobiology 183 (2012) 75-84, Elsevier B.V. 2012.
Kaczka, et al., Effects of lung inflation on airway heterogeneity during histaminergic bronchoconstriction, Journal of Applied Physiology 115: 626-633, 2013, the American Physiological Society, 2013.
Kaczka, et al., Assessment of Time-Domain Analyses for Estimation of Low-Frequency Respiratory Mechanical Properties and Impedance Spectra, Annals of Biomedical Engineering, vol. 23, pp. 135-151, 1995, Biomedical Engineering Society, 1995.
Kaczka, et al., Regional Expansion in Canine Lungs Using Ct Image Registration: A Comparison of Jacobian Determinant and Density Methods, Pulmonary Ventilation Dynamics: Novel Models, Images and Theories, American Journal of Respiratory Critical Care Medicine 183;2011:A3535, 2011.
Kaczka, et al., Effects of high and Low Tidal Volume Ventilation on Respiratory Mechanics and Systemic Inflammation in Canine Acute Lung Injury, Modeling, Mechanics and Gas Exchange, American Journal of Respiratory Critical Care Medicine 185;2012:A2046, 2012.
Kaczka, et al., Multi-Frequency Oscillatory Ventilation Improves Gas Exchange and Lung Recruitment in Preterm Lambs, Novel and Traditional Lung Function Assessment, American Journal of Respiratory Critical Care Medicine 189;2014:A3567, 2014.
Karmrodt, et al., Quantification of atelectatic lung volumes in two different porcine models of ARDS, British Journal of Anaesthesia 97 (6): 883-95 (2006).
Lehr, et al., Photographic measurement of pleural surface motion during lung oscillation, the American Physiological Society, 1985.
Li, et al., Establishing a Normative Atlas of the Human Lung: Intersubject Warping and Registration of Volumetric CT Images, Academy of Radiology 2003: 10:255-265, AUR 2003.
Luecke, et al., Computed tomography scan assessment of lung volume and recruitment during high-frequency oscillatory ventilation, Critical Care Medicine 2005 vol. 33, No. 3, the Society of Critical Care Medicine and Lippincott Williams & Wilkins, 2005.
Adams, et al., Air Trapping and Airflow Obstruction in Newborn Cystic Fibrosis Piglets, American Journal of Respiratory and Critical Care Medicine, vol. 188, American Thoracic Society, 2013.
Adler, et al., GREIT: a unified approach to 2D linear EIT reconstruction of lung images, Institute of Physics and Engineering in Medicine, 2009, UK.
Allan, Patrick F., MD, High-Frequency Percussive Ventilation: Pneumotachograph Validation and Tidal Volume Analysis, Respiratory Care, vol. 55, No. 6, Jun. 2010.
Allan, et al., High-Frequency Percussive Ventilation Revisited, Journal of Burn Care and Research, vol. 31, No. 4, Jul./Aug. 2010.
Allen, et al., Alveolar Pressure Magnitude and Asychrony during High-Frequency Oscillations of Excised Rabbit Lungs, Department of Pediatrics, Harvard Medical School, and The Biomechanics Institute, Boston, Massachusetts, 1985.
Allen, et al., Regional Alveolar Pressure during Periodic Flow, Dual Manifestations of Gas Inertia, The American Society for Clinical Investigation, Inc., vol. 76, Aug. 1985.
Allen, et al., Heterogeneity of mean alveolar pressure during high-frequency oscillations, The American Physiologica Society, 1987.
Amato, et al., Beneficial Effects of the "Open Lung Approach" with Low Distending Pressures in Acute Respiratory Distress Syndrome, American Journal of Respiratory and Critical Care Medicine, vol. 152, 1995.
Amato, et al., Effect of a Protective-Ventilation Strategy on Mortality in the Acute Respiratory Syndrome, The New England Journal of Medicine, vol. 338, No. 6, Massachusetts Medical Society, 1998.
Amini, Reza & Kaczka, David W., Impact of Ventilation Frequency and Parenchymal Stiffness on Flow and Pressure Distribution in a Canine Lung Model, Annals of Biomedical Engineering, The Journal of the Biomedical Engineering Society, vol. 41, No. 12, Dec. 2013.
Amini, et al., Nonlinear Time-Dependent Model of Recruitment and Decrecruitment in Canine Lung Injury, A66 Modeling, Mechanics and Gas Exchange/Thermatic Poster Session, May 20, 2012.
Ranieri, et al., Acute Respiratory Distress Syndrome, The Berlin Definition, JAMA, Jun. 20, 2012, vol. 307, No. 23, American Medical Association, 2012.
Wiedemann, et al., Ventilation with Lower Tidal vols. as compares With Traditional Tidal Volumes For Acute Lung Injury and the Acute Respiratory Distress Syndrome, The New England Journal of Medicine, vol. 342, No. 18, The Massachusetts Medical Society, May 4, 2000.
Armstrong, et al., Distribution of tidal ventilation during volume-targeted ventilation is variable and influenced by age in the preterm lung, Intensive Care Med, Springer and ESICM, 2011.
Attar, Mohammad Ali and Donn, Steven, M., Mechanisms of ventilator-induced long injury in premature Infants, Semin Neonatol 2002; 7:353-360, Elsevier Science, Ltd, 2002.
Awadalla, et al., Early Airway Structural Changes in Cystic Fibrosis Pigs as a Determinant of Particle Distribution and Deposition, Annals of Biomedical Engineering, vol. 42, No. 4, Apr. 2014, Biomedical Engineering Society.
Bagga, et al., Improved compliance with lower tidal volumes for initial ventilation setting-using a Computerized Clinical Decision Support System, Respiratory Care, Daedalus Enterprises, Dec. 10, 2013.
Bates, Jason H. T. and Irvin, Charles G., Time dependence of recruitment and derecruitment in the lung: a theoretical model, J Appl Physiol 93: 705-713, The American Physiological Society, 2002.
Bellerdine-Black, et al., Relationship between dynamic respiratory mechanics and disease heterogeneity in sheep lavage injury, Critical Care Medicine, vol. 35, No. 3, Lippincott Williams & Wilkins 2007.
Bellerdine-Black, et al., Impact of Positive End-Expiratory Pressure During Heterogeneous Lung Injury: Insights from Computed Tomographic Image Functional Modeling, Annals of Biomedical Engineering, vol. 36, No. 6, Jun. 2008.
Bojmehrani, et al., Comparison of usual and alternative methods to measure height in mechanically ventilated patients: potential impact on protective ventilation, Respiratory Care, Nov. 19, 2013, Daedalus Enterprises.
Brower, et al., Higher versus Lower Positive End-Respiratory Pressures in Patients with the Acute Respiratory Distress Syndrome, The New England Journal of Medicine, vol. 351, No. 4, Jul. 22, 2004, Massachusetts Medical Society.
Chakraborty, et al., Acute Lung Injury in Preterm Newborn Infants: Mechanisms and Management, Pediatric Respiratory Reviews 11 (2010) 162-170, Elsevier Ltd., 2010.
Chang, H. K., Mechanisms of gas transport during ventilation by high-frequency oscillation, Brief Review, The American Physiological Society, 1984.
Choi et al., Numerical Study of High-Frequency Oscillatory Air flow and Convective Mixing in a CT-Based Human Airway Model, Annals of Biomedical Engineering, vol. 38, No. 12, Dec. 2010.

(56) References Cited

OTHER PUBLICATIONS

Choi, et al., Registration-based assessment of regional lung function via volumetric CT images of normal subjects vs. severe asthmatics, J Appl Physiol 115: 730-742, 2013, The American Physiological Society, 2013.
Chon, et al., Differences in regional wash-in and wash-out time constants for xenon-CT ventilation studies, Respiratory Physiology & Neurobiology 148 (2005) 65-83, Elsevier B.V., 2005.
Chon, et al., High-Resolution Topographic Distribution of Regional Inflation in Healthy and Injured Canine Lungs, A66 Modeling, Mechanics and Gas Exchange/Thematic Poster Session, Am J Respiratory Critical Care, May 20, 2012.
Chung, et al., High-frequency percussive ventilation and low tidal volume ventilation in burns: A randomized controlled trial, Critical Care Medicine 2010 vol. 38, No. 10, the Society of Critical Care Medicine and Lippincott Williams & Wilkins 2010.
Cioffi, et al., High-frequency percussive Ventilation in Patients with Inhalation Injury, The Journal of Trauma, vol. 29, No. 3, Williams & Wilkins Co. 1989.
Claris, et al., High-frequency oscillatory ventilation, Semin Neonatol 1997: 2: 129-137, W.B. Saunders Company Ltd. 1997.
Clark, et al., Lung injury in neonates: Causes, strategies for prevention, and long-term consequences, Medical Progress, The Journal of Pediatrics, vol. 139, No. 4, Mosby, Inc. 2001.
Clark, et al., Prospective Randomized Comparison of High-Frequency Oscillatory and Conventional Ventilation in Respiratory Distress Syndrome, Pediatrics vol. 89 No. 1 Jan. 1992, The American Academy of Pediatrics 1992.
Clark, et al., Ventilation-Perfusion Matching in Large and Small Mammals, 866 Novel and Traditional Lung Function Assessment, May 19, 2014, Am J. Respiratory Critical Care Medicine, 2014.
Colletti, et al., Simulating ventilation distribution in heterogenous lung injury using a binary tree data structure, Computers in Biology and Medicine 41 (2011) 936-945, Elsevier, Ltd, 2011.
Colletti, et al., Simulating Gas Exchange in The Canine Lung Using Computational Modeling, A61 Modeling Lung Structure and Function/ Thermatic Poster Session, Am J. Respir Critical Care Medicine, May 19, 2013.
Cools, et al., Elective high frequency oscillatory ventilation versus conventional ventilation for acute pulmonary dysfunction in preterm infants, The Cochrane Collaboraton, John Wiley & Sons, Ltd. 2010.
Cools, et al., Elective high-frequency oscillatory versus conventional ventilation in preterm infants: a systematic review and meta-analysis of individual patients' data, The Lancet vol. 375, Jun. 12, 2010.
Dellaca, et al., Assessment of Dynamic Mechanical Properties of the Respiratory System During High-Frequency Oscillatory Ventilation, vol. 41, No. 11, The Society of Critical Care Medicine and Lippincott Williams & Wilkins, Nov. 2013.
Derdak, et al., High-Frequency Oscillatory Ventilation for Acute Respiratory Distress Syndrome in Adults, American Journal of Respiratory and Critical Care Medicine, vol. 166, 2002.
Derdak, Stephen, High-frequency oscillatory ventilation for acute respiratory distress syndrome in adult pateints, Critical Care Medicine 2003 vol. 31, No. 4, Lippincott Williams & Wilkins, 2003.
Derdak, Stephen, High-frequency oscillatory ventilation for adult acute respiratory distress syndrome: A decade of progress, Critical Care Medicine 2005 vol. 33, No. 3, The Society of Critical Care Medicine and Lippincott Williams & Wilkins, 2005.
Ding, et al., Comparison of image registration based measures of regional lung ventilation from dynamic spiral CT with Xe-Ct, Med. Phys. 39 (8), Aug. 2012, American Association Physiological Medicine 2012.
Donn, et al., Can mechanical ventilation strategies reduce chronic lung disease, Seminars in Neonatology, Elsevier Ltd., 2003.
Dreyfuss, et al., Critical Care Perspective on the Physiologic and Clinical Relevance of Lung-borne Cytokines during Ventilator-induced Lung injury, American Journal of Respiratory Critical Care Medicine, vol. 167, 2003.
Du, et al., Reproducibility of registration-based measures of lung tissue expansion, Medical Physics, The International Journal of Medical Physics Research and Practice, Mar. 21, 2012.
Easley, et al., Total and regional lung volume changes during high-frequency oscillatory ventilation (HFOV) of the normal lung, Respiratory Physiology & Neurobiology 165 (2009) 54-60, Elsevier B.V 2008.
Ferguson, et al., High-Frequency Oscillation in Early Acute Respiratory Distress Syndrome, The New England Journal of Medicine, vol. 368, No. 9, Massachusetts Medical Society, Feb. 28, 2013.
Fessley, et al., Protocols for lung protective ventilation, Critical Care Medicine, vol. 33, No. 3, Society of Critical Care Medicine and Lippincott Williams & Wilkins, 2005.
Fessley, et al., Does High-Frequency Ventilation Offer Benefits Over Conventional Ventilation in Adult Patients With Acute Respiratory Distress Syndrome? Respiratory Care, vol. 52, No. 5, May 2007.
International Search Report and Written Opinion dated Jul. 11, 2016 for counterpart PCT Application No. PCT/US2016/030637.
Luecke, et al., Oleic Acid vs Saline Solution Lung Lavage-Induced Acute Injury, Effects on Lung Morphology, Pressure-Volume Relationships, and Response to Positive End-Expiratory Pressure, Chest, Original Research, Critical Care Medicine, American College of Chest Physicians, 2006.
Luna, et al., High-Frequency Oscillatory Ventilation Combined with Volume Guarantee in a Neonatal Animal Model of Respiratory Distress Syndrome, Critical Care Research and Practice, vol. 2013, Hindawi Publishing Corporation, 2013.
Mondonedo, et al., Volatile anesthetics and the treatment of severe bronchospasm: a concept of targeted delivery, Drug Discovery Today: Disease Models (2014), Elsevier Ltd. 2014.
Muellenbach, et al., High-frequency oscillatory ventilation reduces lung inflammation: a large-animal 24-h model of respiratory distress, Intensive Care Med (2007) 33:1423-1433, Springer-Verlag 2007.
Mulreany, et al., Volumetric Xenon-CT Imaging of Conventional and High-frequency Oscillatory Ventilation, Academy of Radiology 2009; 16:718-725, AUR, 2009.
Nuckton, et al., Pulmonary Dead-Space Fraction As a Risk Factor for Death in the Acute Respiratory Distress Syndrome, New England Journal of Medicine, vol. 346, No. 17, Apr. 25, 2002, Massachusetts Medical Society, 2002.
Ogawa, et al., A multicenter randomized trial of high frequency oscillatory ventilation as compared with conventional mechanical ventilation in preterm infants with respiratory failure, Early Human Development, 32 (1993) 1-10, Elsevier Scientific Publishers Ireland Ltd., 1993.
Ortiz, et al., Extracorporeal Membrane Oxygenation in Pediatric Respiratory Failure, Pediatric Clinics of North American, vol. 34, No. 1, Feb. 1987.
Osborn, et al., Randomized Trial of High-Frequency Oscillatory Ventilation Versus Conventional Ventilation: Effect on Systemic Blood Flow in Very Preterm Infants, Mosby, Inc. 2003.
Pan, et al., Estimation of regional lung expansion via 3D image registration, Medical Imaging 2005: Physiology, Function and Structure from Medical Images, Proceedings of SPIE vol. 5746 (SPIE, Bellingham, WA, 2005).
Pellicano, et al., Comparison of four methods of lung volume recruitment during high frequency oscillatory ventilation, Intensive Care Medicine (2009) 35:1990-1998, Springer and ESICM 2009.
Pillow, et al., In Vitro Performance Characteristics of High-Frequency Oscillatory Ventilators, American Journal of Respiratory Critical Care vol. 164. pp. 1019-1024, 2001.
Pillow, et al., Effects of Gestation and Antenatal Steroid on Airway and Tissue Mechanics in Newborn Lambs, American Journal of Respiratory Critical Care Medicine vol. 163. pp. 1158-1163, 2001.
Pillow, et al., Dependence of Intrapulmonary Pressure Amplitudes on Respiratory Mechanics during High-Frequency Oscillatory Ventilation in Preterm Lambs, Pediatric Research, vol. 52, No. 4, 2002, International Pediatric Research Foundation, Inc. 2002.
Pillow, et al., Monitoring of lung volume recruitment and derecruitment using oscillatory mechanics during high-frequency oscillatory ventilation in the preterm lamb, Pediatric Critical Care Medicine

(56) References Cited

OTHER PUBLICATIONS 2004, vol. 5, No. 2, Society of Critical Care Medicine and World Federation of Pediatric Intensive and Critical Care Societies, 2004.
Pillow, et al., High-frequency oscillatory ventilation: Mechanisms of gas exchange and lung mechanics, Critical Care Medicine 2005, vol. 33, No. 3, Lippincott Williams & Wilkins 2005.
Pillow, Jane J., Tidal volume, recruitment and compliance in HFOV: same principles, different frequency, European Respiratory Journal, vol. 40, No. 2, 2012.
Polgase, et al., Pressure-versus volume-limited sustained inflations at resuscitation of premature newborn lambs, BMC Pediatrics 2014, 14:43.
Reinhardt, et al., Registration-based estimates of local lung tissue expansion compared to xenon CT measures of specific ventilation, Medical Image Analysis 12 (2008) 752-763, Elsevier B.V. 2008.
Rettwitz-Volk, et al., A prospective, randomized, multicenter trial of high-frequency oscillatory ventilation compared with conventional ventilation in preterm infants with respiratory distress syndrome receiving surfactant, The Journal of Pediatrics, Feb. 1998, Mosby, Inc. 1998.
Rubenfeld, et al., Incidence and Outcomes of Acute Lung Injury, The New England Journal of Medicine 2005; 353:1685-93, Oct. 20, 2005, Massachusetts Medical Society 2005.
Salim, et al., High-frequency percussive ventilation, Critical Care Medicine 2005 vol. 33, No. 3, The Society of Critical Care Medicine and Lippincott Williams & Wilkins, 2005.
Schoene, et al., Pathophysiological patterns of resolution from acute oleic acid lung injury in the dog, the American Pathological Society, 1984.
Schuster, Daniel P., State of the Art: ARDS: Clinical Lessons from the Oleic Acid Model of Acute Lung Injury, American Journal of Respiratory and Critical Care Medicine, vol. 149, 1994.
Simon, et al., Parameter estimation and confidence intervals for Xe-CT ventilation studies: a Monte Carlo approach, modeling in physiology, the American Physiological Society, 1998.
Slutsky, et al., Ventilator-Induced Lung Injury, The New England Journal of Medicine, 369;22, Nov. 28, 2013, Massachusetts Medical Society, 2013.
Stoltz, et al., Intestinal CFTR expression alleviates meconium ileus in cystic fibrosis pigs, Technical Advance, The Journal of Clinical Investigation, vol. 123, No. 6, Jun. 2013.
Sud, et al., High frequency oscillation in patients with acute lung injury and acute respiratory distress syndrome (ARDS): systematic review and meta-analysis, BMJ 2010; 340:c2327, Apr. 2010.
Tawhai, et al., CT-based geometry analysis and finite element models of the human and ovine bronchial tree, Journal of Applied Physiology 97: 2310-2321, 2004, the American Physiological Society, 2004.
Tawhai, et al., An Imaging-based Computational Approach to Model Ventilation Distribution and Soft-tissue Deformation in the Ovine Lung, SPIE, Academy of Radiology 2006; 13:113-120, AUR 2006.
Tawhai, et al., The lung physiome: merging imaging-based measures with predictive computational models, Advanced Review, WIREs Syst Biol Med 2009, vol. 1, Jul./Aug. 2009, John Wiley & Sons, Inc. 2009.
Thome, et al., Randomized comparison of high-frequency ventilation with high-rate intermittent positive pressure ventilation in preterm infants with respiratory failure, The Journal of Pediatrics, Jul. 1999, Mosby, Inc. 2009.
Tingay, et al., Surfactant before the first inflation at birth improves spatial distribution of ventilation and reduces lung Injury in preterm lambs, Journal of Applied Physiology 116: 251-258, 2014, the American Physiological Society 2014.
Tingay, et al., Indicators of Optimal Lung Volume During High-Frequency Oscillatory Ventilation in Infants, Critical Care Medicine, the Society of Critical Care Medicine and Lippincott Williams & Wilkins 2013.
Tingay, et al., Effect of sustained inflation vs. stepwise PEEP strategy at birth on gas exchange and lung mechanics in preterm lambs, Articles/Translational Investigation, Pediatric Research, vol. 75, No. 2, Feb. 2014, International Pediatric Research Foundation, Inc. 2014.
Tschirren, et al., Intrathoracic Airway Trees: Segmentation and Airway Morphology Analysis From Low-Dose CT Scans, IEEE Transactions on Medical Imaging, vol. 24, No. 12, Dec. 2005.
Tschirren, et al., Matching and Anatomical Labeling of Human Airway Tree, IEEE Transactions on Medical Imaging, vol. 24, No. 12, Dec. 2005.
Van Heerde, et al., Spontaneous breathing during high-frequency oscillatory ventilation improves regional lung characteristics in experimental lung injury, Acta Anaesthesio Scand 2010; 54: 1248-1256, The Acts Anesthesiologica Scandinavica Foundation 2010.
Venegas, et al., A general dimensionless equation of gas transport by high-frequency ventilation, the American Physiological Society, 1986.
Venegas, et al., Understanding the pressure cost of ventilation: Why does high-frequency ventilation work? Critical Care Medicine, vol. 22, No. 9, Williams & Wilkins 1994.
Wellek, et al., On the Proper Use of the Crossover Design in Clinical Trials, Medicine, Review Article, Deutsches Aerzteblatt International, 2012; 109(15): 276-81.
Wolf, et al., Noninvasive assessment of lung volume: Respiratory inductance plethysmography and electrical Impedance tomography, Critical Care Medicine 2005 vol. 33, No. 3, the Society of Critical Care Medicine and Lippincott Williams & Wilkins, 2005.
Yin, et al., Mass preserving nonrigid registration of CT lung images using cubic B-spline, Med. Phys. 36 (9), Sep. 2009, American Association of Physicists in Medicine 2009.
Yin, et al., Lung Lobar Slippage Assessed with the Aid of Image Registration, Med Image Comput Assist Interv. 2010; 13(Pt 2): 578-585, Springer-Verlag Berlin Heidelberg 2010.
Yin, et al., A multiscale MDCT image-based breathing lung model with time-varying regional ventilation, Journal of Computational Physics 244 (2013) 168-192, Elsevier, Inc. 2012.
Young, et al., High-Frequency Oscillation for Acute Respiratory Distress Syndrome, the New England Journal of Medicine, Feb. 28, 2013, Massachusetts Medical Society 2013.
Zannin, et al., Optimal mean airway pressure during high-frequency oscillatory ventilation determined by measurement of respiratory system reactance, Basic Science Investigation, Articles, Pediatric Research, vol. 75, No. 4, Apr. 2014, International Pediatric Research Foundation, 2014.
Zick, et al., Effect of PEEP and Tidal Volume on Ventilation Distribution and End-Expiratory Lung Volume: A Prospective Experimental Animal and Pilot Clinical Study, PLOS One, vol. 8, Issue 8, Aug. 2013.
David W. Kaczka, et al.—U.S. Appl. No. 14/511,590, filed Oct. 10, 2014.
Office Action issued by the European Patent Office dated Jan. 28, 2019 for counterpart European Patent Application No. 16 722 024.3.
Amini, et al., Effects of Intratidal Overdisention and Derecruitment on Global Lung Mechanics: A Simulation Study—Date unknow but prior to U.S. filing date.
Chon, et al., Effect of Lung Inflation on Canine Airway Dimensions in vivo—Date unknown but prior to U.S. filing date.
European Office Action dated Feb. 20, 2020 for counterpart European Patent Application No. 16722024.3.

\* cited by examiner

Single-Frequency Oscillatory Ventilation

Multi-Frequency Oscillatory Ventilation

SYSTEMS AND METHODS FOR MULTI-FREQUENCY OSCILLATORY VENTILATION

CROSS-REFERENCE TO RELATED APPLICATIONS

This application claims priority to U.S. Provisional Application 62/163,737 filed on May 19, 2015 the contents of which are hereby incorporated by reference herein.

GOVERNMENT LICENSE RIGHTS

This invention was made with government support under Grant No. UM1HL108724 awarded by the National Institutes of Health. The government has certain rights in the invention.

COPYRIGHT STATEMENT

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

This disclosure relates generally to ventilators for supplying gas to facilitate and support respiration, and particularly to ventilators which employ multi-frequency ventilation with specifically tuned frequencies and amplitude and phase control over the applied waveform.

BACKGROUND

Respiratory failure from acute respiratory distress syndrome (ARDS) is associated with high mortality acutely (up to 40%), and accounts for about 4 million ICU days annually in the U.S. ARDS survivors have substantial morbidity, and may have long-term physical and mental health impairments. ARDS imposes significant burdens on public health resources worldwide, and only minimal improvements in outcomes have occurred over recent decades.

Risks for developing ARDS include a diverse range of predisposing factors and initiating insults, such aspiration, pneumonia, trauma, sepsis, pancreatitis, inhalation injury, transfusion, and burns. Regardless of etiology, ARDS results in progressive deterioration in lung function towards a final common pathway: respiratory failure characterized by alveolar flooding, derecruitment, reduced compliance, increased shunting and dead space, and life-threatening hypoxemia. A key pathologic feature of ARDS is the heterogeneity of local injury severity and regional mechanical properties.

The mainstay of treatment for ARDS is endotracheal intubation and conventional mechanical ventilation (CMV). However CMV may exacerbate existing lung injury, due to cyclic, intratidal overdistension and repeated, asynchronous opening and closing of airways with each inflation. The mechanical stresses associated with these phenomena result in the release of cytokines and other inflammatory mediators that may exacerbate lung injury. This ventilator-associated lung injury (VALI) is thus a direct result of the mechanical heterogeneity of injured parenchyma, leading to maldistribution of ventilation and corresponding impairments in gas exchange.

Ventilation strategies that limit this end-expiratory derecruitment and end-inspiratory overdistension are the only interventions to have significantly reduced the morbidity and mortality of ARDS, using appropriate levels of positive end expiratory pressure (PEEP) to limit end-expiratory opening and closing and low tidal volumes (VT's) to reduce inspiratory overdistension. Such 'protective' ventilation strategies, however, may result in significant hypoventilation of the injured lung, due to increased deadspace and ventilation to perfusion ratio ($\dot{V}/\dot{Q}$) abnormalities. Most lung protective strategies for ventilator management use algorithmic, 'one size fits all' approaches, based on height, weight, or global arterial oxygenation. Adjustments to VT or PEEP based on such criteria provide little insight into how such interventions impact regional gas transport in the injured lung, or how to customize a ventilator management strategy for an individual patient's pathophysiology. For example, the optimal level of PEEP depends much more on the unique pattern of injury and amount of recruitable lung, rather than on oxygenation alone.

There is a continuing need for improvement in ventilation techniques to treat a variety of lung conditions and injuries.

SUMMARY

The present invention relates to systems and methods for improving lung function and gas exchange. Volume oscillations are applied at multiple frequencies substantially simultaneously, rather than at a single high frequency, to provide more even distribution of ventilation to different lung regions in accordance with local mechanical properties. Ventilating an injured lung with a broadband waveform, for example, optimizes gas transport to the periphery, and thereby improves oxygenation and $\dot{V}/\dot{Q}$ matching. 'Multi-Frequency Oscillatory Ventilation' (MFOV) is specifically configured to complement the heterogeneous mechanics of the injured lung. In effect, MFOV allows the local impedances of the injured parenchyma to selectively filter out flows of less-desirable' frequencies, and allows flows at frequencies more effective for a particular region to participate in gas exchange. With further adjustments in oscillatory pressure amplitude and mean airway pressure, MFOV improves gas exchange in the injured lung while minimizing the detrimental effects of cyclic alveolar overdistension and derecruitment.

In one implementation, a system is described with an oscillatory ventilator configured for oscillating at plurality of specifically tuned frequencies simultaneously a ventilation gas for delivery to a pulmonary region of a patient. A ventilator control system, in communication with the oscillatory ventilator, controls a waveform input for the oscillatory ventilator. The waveform input comprises the plurality of specifically tuned frequencies, and an amplitude and a phase associated with each frequency that is alterable in response to physical or physiologic changes in the patient. A sensor can be provided for measuring the ventilation gas being delivered to a pulmonary region of the patient and providing the measurement to the ventilator control system for use in producing the waveform.

DETAIL DESCRIPTION

Figure 1A:
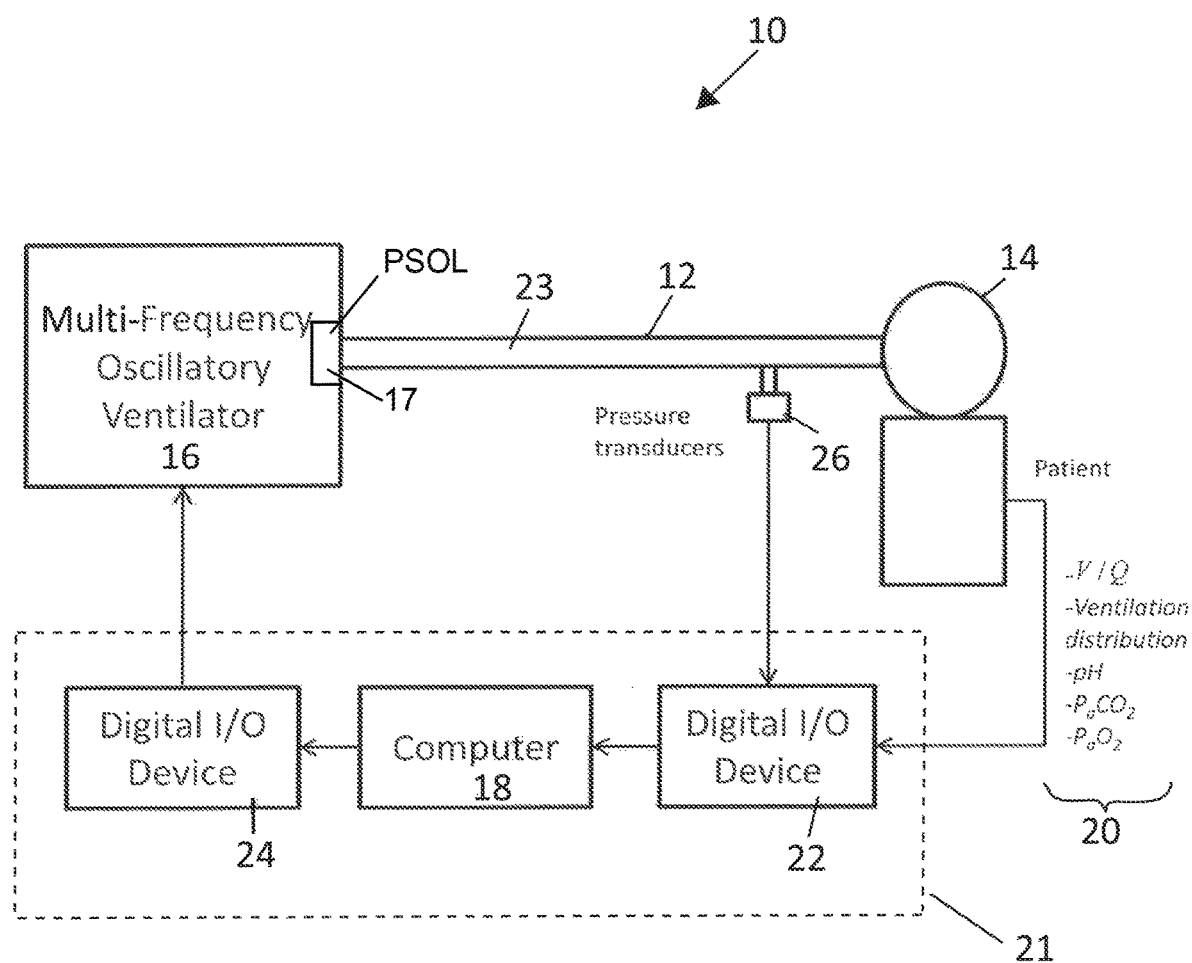
FIG. 1A shows an MFOV system in accordance with preferred embodiments of the invention.
Figure 1B:
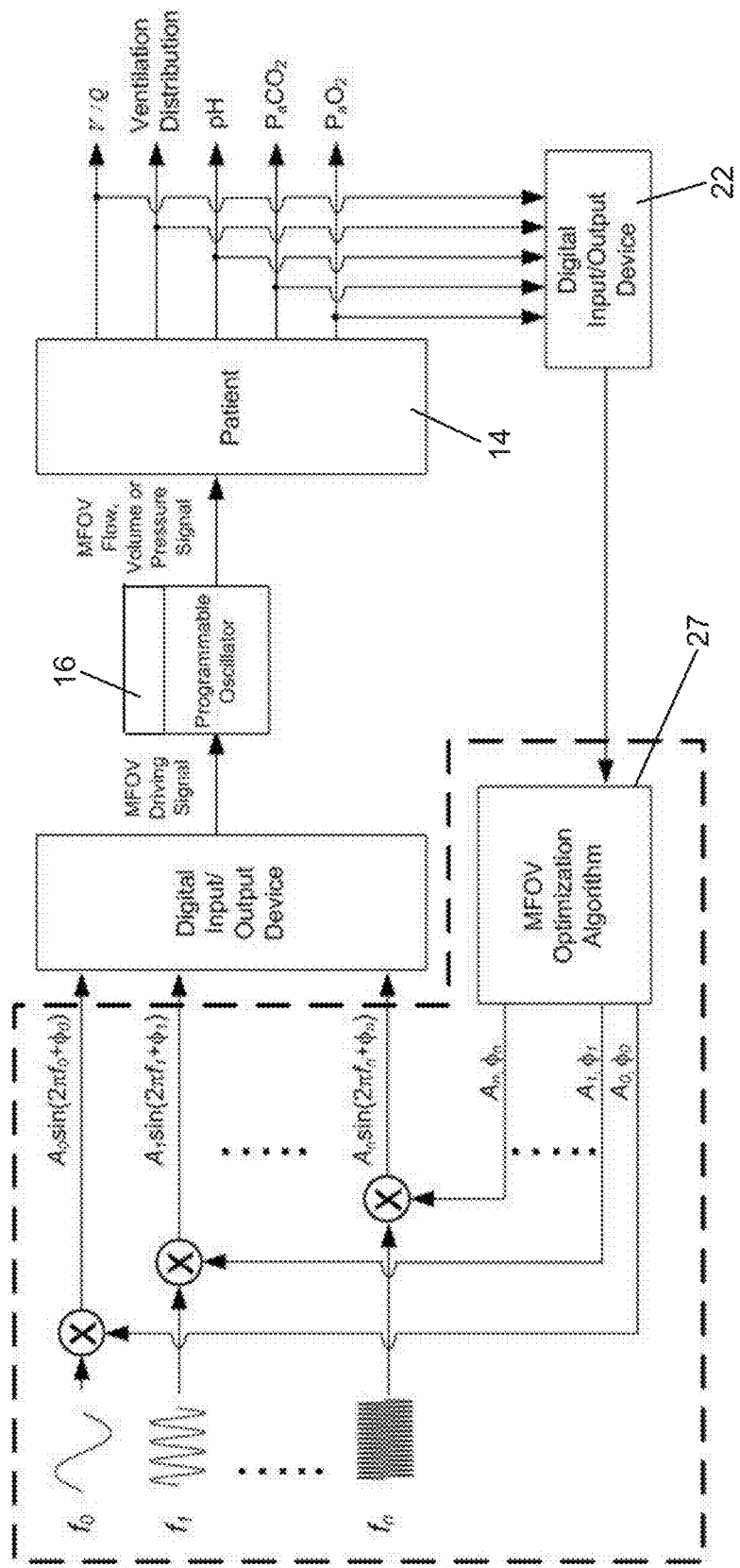
FIG. 1B schematically illustrates a system for controlling delivery of multi-frequency therapeutic ventilation to a patient.

The present invention relates to combinations of oscillatory frequencies, amplitudes, and phases by which multi-frequency oscillatory ventilation (MFOV) can support gas exchange. MFOV relates to ventilation frequency for gas exchange that varies from region-to-region, depending on gravity, airway branching, and local mechanical properties of the tissue. Ventilator system 10 includes an oscillatory ventilator 16 to deliver ventilation gas 23 under pressure to the airway of a patient 14 as shown generally in FIG. 1A. The ventilator system 10 can include an oscillatory ventilator 16 operative to apply one or more specifically tuned frequencies to the gas delivered through tubing system 12 to the patient 14. Specifically tuned frequencies may be each determined and applied independent of each other, which means that they can each be fundamental frequencies, as opposed to a single fundamental frequency and multiple harmonic frequencies. Physiological characteristics 20 (e.g. $\dot{V}/\dot{Q}$, Ventilation Distribution, pH, $P_aCO_2$, and $P_aO_2$) can be measured on the patient 14 with corresponding sensors and operating characteristics (e.g. gas pressure) can measured by one or more transducers 26. The measurements can be delivered to input device 22 (if the measurements are in analog form, input device 22 can include an analog to digital convertor). The data from input device 22 is received by a computer 18 for recordal and selectively used with an output device 24 to control the operation of oscillatory ventilator 16. The computer 18 executes stored software/firmware to control the operating parameters of oscillatory ventilator 16, including the frequencies generated by the oscillatory ventilator 16, as shown schematically in FIG. 1B and FIG. 2. The software can include optimization software 27 to control the amplitude and phase characteristics of the applied waveform input (shown in FIG. 2). This can be done digitally, as shown, with digitally implemented signal generators for producing n-waveforms each with a frequency, phase, and amplitude. As the airways of each lung have unique heterogeneous features, the different frequencies applied during a therapeutic sequence can treat different regions simultaneously. The applied frequencies can be staggered or temporally offset by a time (t) or simultaneously applied to treat different conditions. In accordance with certain implementations, one or more therapeutic drugs may be entrained within the gas flow to enable direct treatment of affected organs, or properties of the gas flow including, but not limited to, moisture level may be altered to effect positive therapeutic outcomes in the patient.

Ventilator system 10 can be implemented with any type of ventilator or oscillator, and for low frequency ventilation or high frequency ventilation. The frequency levels for high frequency ventilation compared to low frequency ventilation depends on a number of factors including the species, the alveolar ventilation of the species, and the volume of the conducting airways. The transition from low frequency ventilation to high frequency ventilation is defined as: $f_t=5*(V'_A/V_D)$; where $V'_A$ is the alveolar ventilation of the species, and $V_D$ is the anatomic dead space volume (i.e., the volume of the conducting airways).

Figure 3:
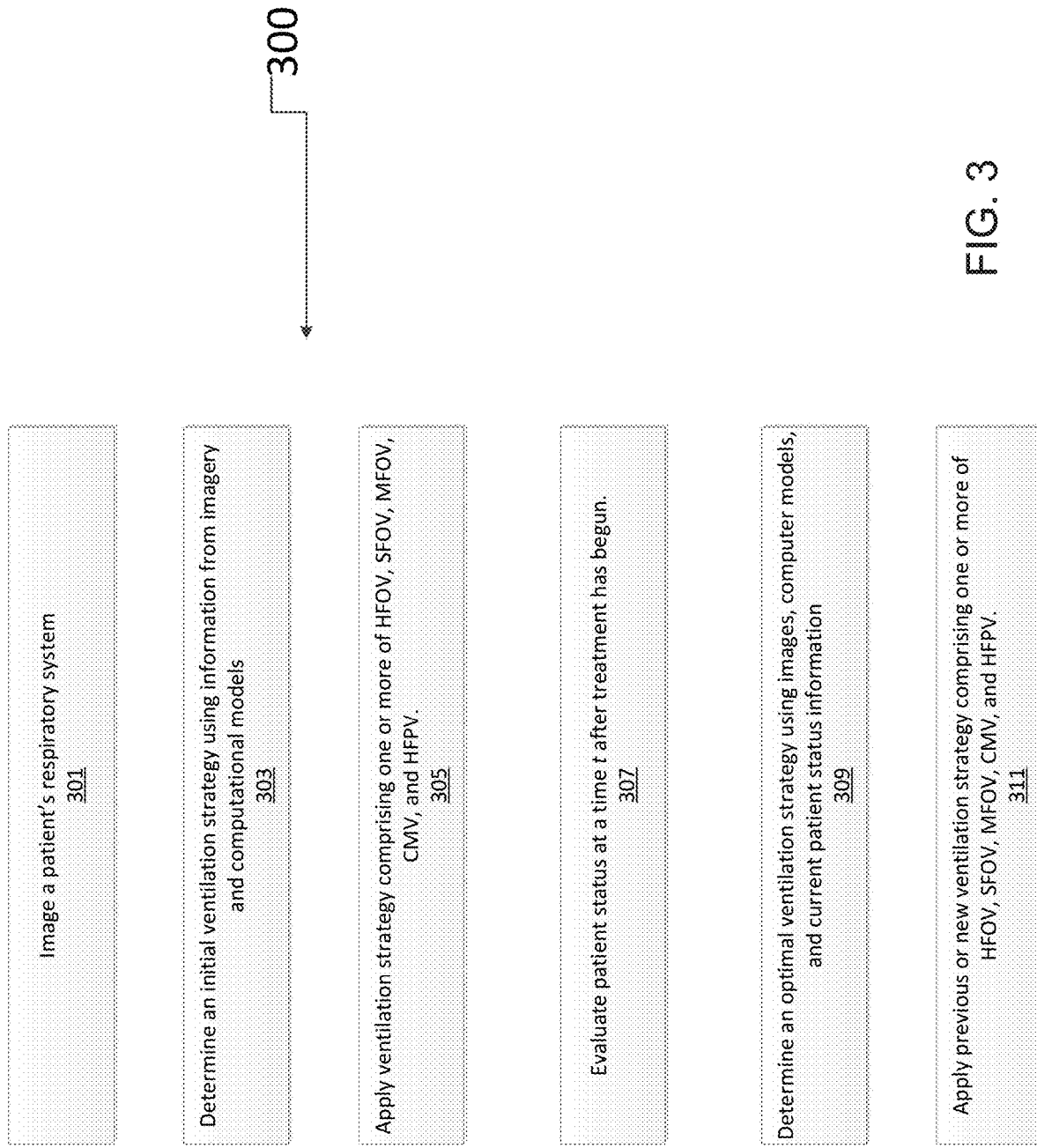
FIG. 3 illustrates a method of treating a patient using a hybrid MFOV system in accordance with various embodiments.

FIG. 3 illustrates a method 300 of treating lung injury or disease in a patient 14. Using, for example but not limited to, CT imaging or EIT, the practitioner may image 301 a patient's 14 respiratory system. With the information gathered from this imagery, the practitioner can determine 303 an initial ventilation strategy by combining the imagery with computational models. The models and related methods enable the practitioner to apply 305 a ventilation strategy comprising one or more of high-frequency oscillatory ventilation (HFOV), single-frequency oscillatory ventilation (SFOV), MFOV, conventional mechanical ventilation (CMV), and high-frequency percussive ventilation (HFPV).

After the patient 14 has been treated for a suitable period of time, the practitioner may evaluate 307 the patient's status. Evaluation of the patient 14 may include additional imagery, visually assessment of the patient 14, or acquisition of patient 14 output values such as blood pH, $HCO_3^-$, $P_aCO_2$, $P_aO_2$, and $S_pO_2$. Based on the results of the evaluation, the practitioner may determine 309 an optimal ventilation strategy using images, computer models, and current patient status information. The optimal ventilation strategy may be the same or different from the initial ventilation strategy. The practitioner can choose to apply 311 the previous ventilation strategy or a new ventilation strategy comprising one or more of HFOV, SFOV, MFOV, CMV, and HFPV.

Mathematical models of biological systems are useful for defining complex relationships between variables and their effects on outcomes, predicting behavior over ranges of conditions, and helping design better experiments. MFOV assumes that the ideal ventilation frequency for gas exchange in the lung will vary from region-to-region, depending on gravity, airway branching, and local mechanical properties. The design of optimal MFOV waveforms in the injured lung thus requires an understanding of the relationship between heterogeneous lung injury and regional ventilation distribution. Advective and diffusive ventilation distribution to the parenchyma under varying degrees of heterogeneous lung injury are simulated using various computational models, incorporating specific three-dimensional information for individual airway and vascular segments. Nodes in the airway tree will account for the viscous dissipation and advective acceleration of gas flow in cylindrical airway conduits, as well as viscoelastic airway walls and parenchymal tissues. To assess regional ventilation to individual acini in the model, the entire tree is traversed using a recursive flow divider algorithm. An example of such an algorithm can be found in Amini, et al., "Intratidal Overdistention and Derecruitment in the Injured Lung: A Simulation Study," Manuscript Submitted to IEEE on Dec. 4, 2015, the contents of which are hereby incorporated by reference herein. Corresponding spatial distributions of acinar pressures and flows are simulated throughout the lung for various MFOV waveforms. Since a portion of the MFOV waveform will be lost to gas compression and airway wall distention, the amount of flow available for 'useful' ventilation at the alveoli will be limited. Such flow losses will not be uniformly distributed across the lung, and will depend on the geometry of airway branching, frequency of oscillations, as well as gravity and local mechanical properties in this heterogeneously injured lung model. Nonlinear alterations in regional impedance are assumed to arise from cyclic variations in airway size, parenchymal strain-stiffening, and acinar recruitment/derecruitment. Acini are allowed to transition between recruited and derecruited states when exposed to stochastically-determined critical opening and closing pressures, respectively. The amplitude and phase components of various MFOV waveforms presented to the computational lung model are iteratively adjusted, using a nonlinear gradient search technique. Several robust optimization criteria are employed, including the distribution widths of net acinar ventilation, $\dot{V}/\dot{Q}$ ratios, regional alveolar pressures and strains, as well as steady-state values for $P_aO_2$, $P_aCO_2$, and pH. Implementation of the algorithm in three dimensions allow for the identification of those anatomic regions that benefit the most from specific MFOV frequencies, as well as those regions which may experience overdistention or atelectrauma. These simulations are used to recommend and augment global strategies for MFOV management, based on the mechanics and recruitment patterns of injured lungs.

Figure 4:
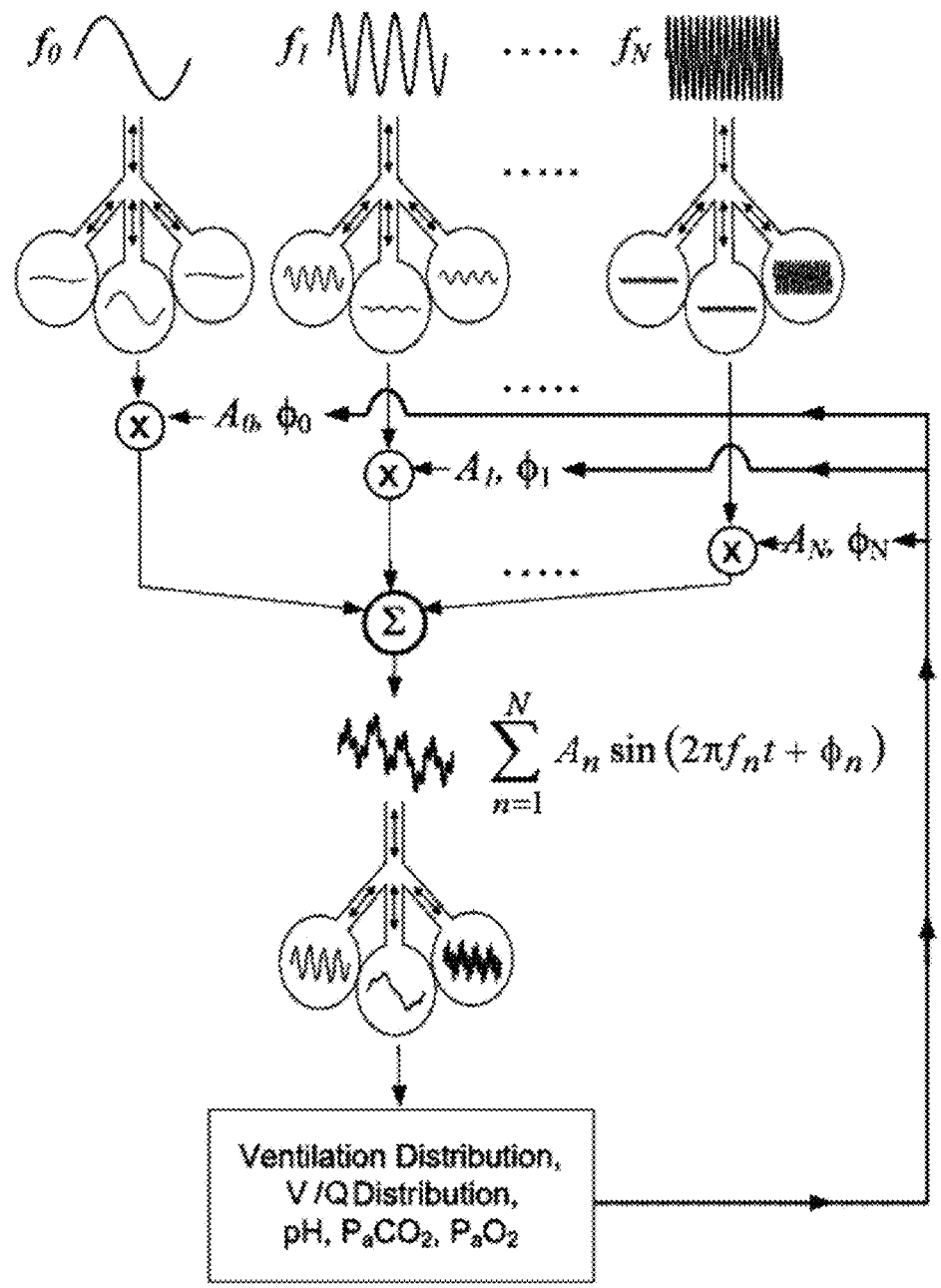
FIG. 4 schematically illustrates amplitude and phase control of MFOV waveforms.

Turning to FIG. 4, each MFOV waveform input can be constructed using up to N sinusoids with different amplitude, frequency, and phase components ($A_n$, $f_n$, and $\Phi_n$, respectively). Each component that contributes to the overall MFOV waveform input may be substantially constant over the treatment regimen or may change with time, and the composition of the MFOV waveform input itself (including the number of sinusoids) may change over time. These changes may be prescribed in advance and specifically tuned as part of a multi-step treatment program, or the changes may be made in response to visual observations of patient 14 status or measured physical indicators of patient 14 status including blood pH, $HCO_3^-$, $P_aCO_2$, $P_aO_2$, and $S_aO_2$.

Figure 5:
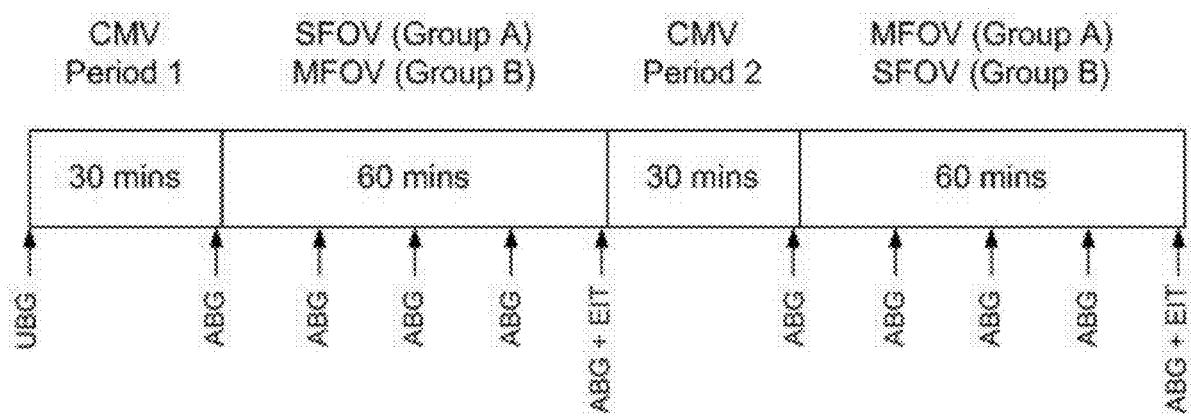
FIG. 5 illustrates the use of different ventilator frequency modes including conventional, high-frequency, and multi-frequency modes.

The multi-frequency method can be used with conventional ventilation (CMV), with single (high) frequency and multi-frequency periods which can be monitored by selected measurement techniques as described herein and as shown in FIG. 5. According to various embodiments, a treatment regimen may comprise alternating periods of CMV, SFOV, and/or MFOV. The SFOV and MFOV treatments in any given period may have substantially constant frequency, amplitude, and phase components or these components may change within or between periods. According to certain embodiments, a given period may comprise more than one technique simultaneously, i.e., CMV may be provided at the same time as SFOV or MFOV.

Figure 6:
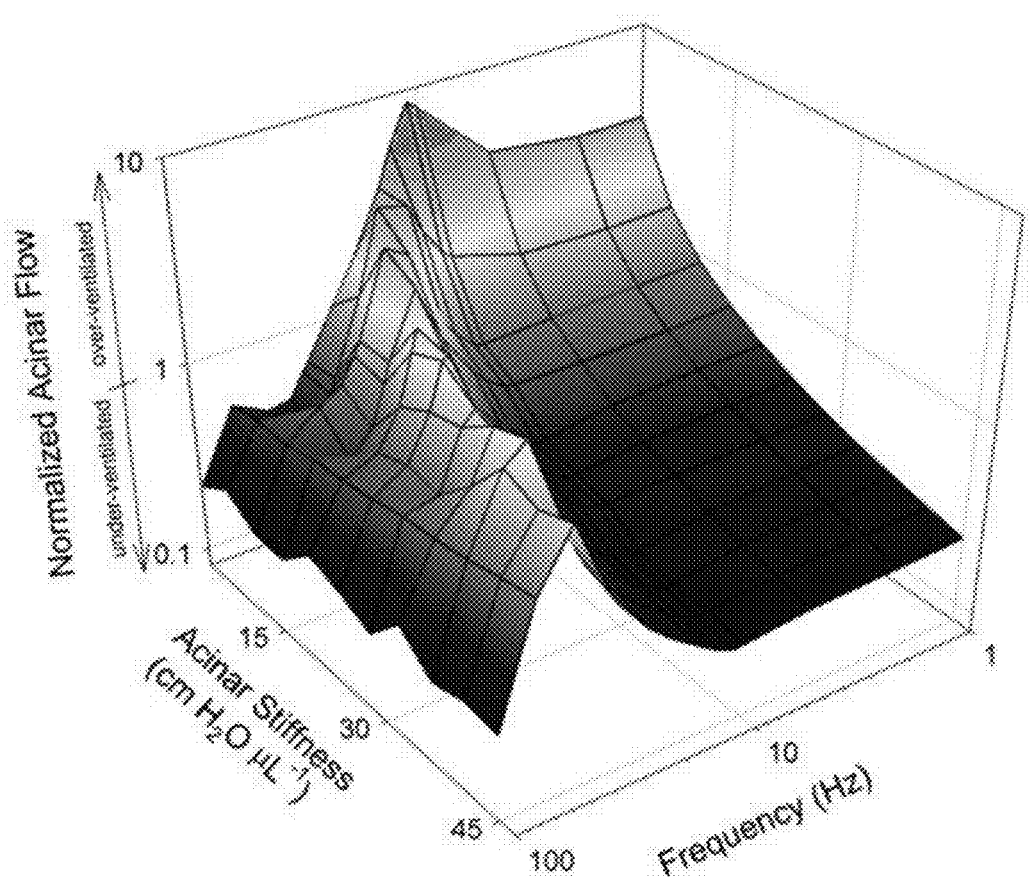
FIG. 6 illustrates acinar flow as a function of frequency and tissue stiffness.

It is difficult to determine the influence of certain factors on the wide distribution of acinar flows and pressures in an injured lung. Mathematical models of biological systems are useful for defining complex relationships between variables and their effects on outcomes, and for predicting behavior over ranges of conditions. Thus, computational modeling can be used for MFOV waveforms in the injured lung, to simulate the complex relationship between mechanical heterogeneity and regional ventilation distribution. High-fidelity computational models of mammalian lungs are used for predicting gas transport and exchange during MFOV. Turning to FIG. 6, normalized acinar flow is illustrated as a function of both frequency and tissue stiffness. In accordance with various embodiments, the acinar flow can be modeled and simulated using an asymmetric, binary-tree data structure with terminal tissue elements corresponding to heterogeneously injured lung tissue. By determining acinar stiffness through computational modeling and imaging of the patient's 14 respiratory system, the model of normalized acinar flow illustrated in FIG. 6 can be used to determine the optimal frequency to strike a balance between under-inflation and over-ventilation. Additional details regarding modeling in mammalian systems is described in Amini et al., "Impact of Ventilation Frequency and Parenchymal Stiffness on Flow and Pressure Distribution in a Canine Lung Model", Annals of Biomedical Engineering, Vol. 41, No. 12 (2013), pp. 2699-2711, the entire contents of which is incorporated herein by reference.

Figures 7A, 7B:
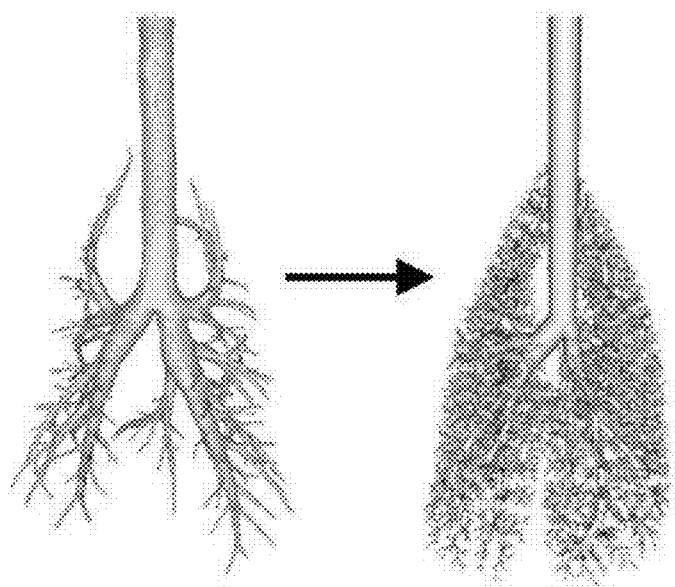
FIGS. 7A and 7B illustrate a computed tomography image and a 3D model of a lung including peripheral airways.

Computational lung models and a recursive flow divider method are combined to simulate advective and diffusive ventilation distribution to the parenchyma under varying degrees of heterogeneous lung injury. Three-dimensional information for individual airway and vascular segments using a database of whole-lung high resolution CT images in healthy and injured mammalian lungs, as well as newly acquired CT images can be utilized. An example of a segmented airway tree obtained from a CT image of a dog lung inflated to 35 cm H2O is shown in FIG. 7A. Details for methods of CT image utilization can be found in Black, et al., "Impact of Positive-End Expiratory Pressure During Heterogeneous Lung Injury: Insights from Computed Tomographic Image Functional Modeling," Annals of Biomedical Engineering, Vol. 36, No. 6, Jun. 2009, pp. 980-991, the entire contents of which is incorporated herein by reference. These images will allow us to develop an airway tree down to diameters of 3 mm. Smaller airways may be modeled using a CT image-based space-filling method. This method allows the use of a greater number of distal airways down to the level of the terminal bronchi within distinct lobular sections. An example of the use of the space-filling method to flesh out peripheral airways in a 3-D model reconstruction of a lung is shown in FIG. 7B.

Figure 8:
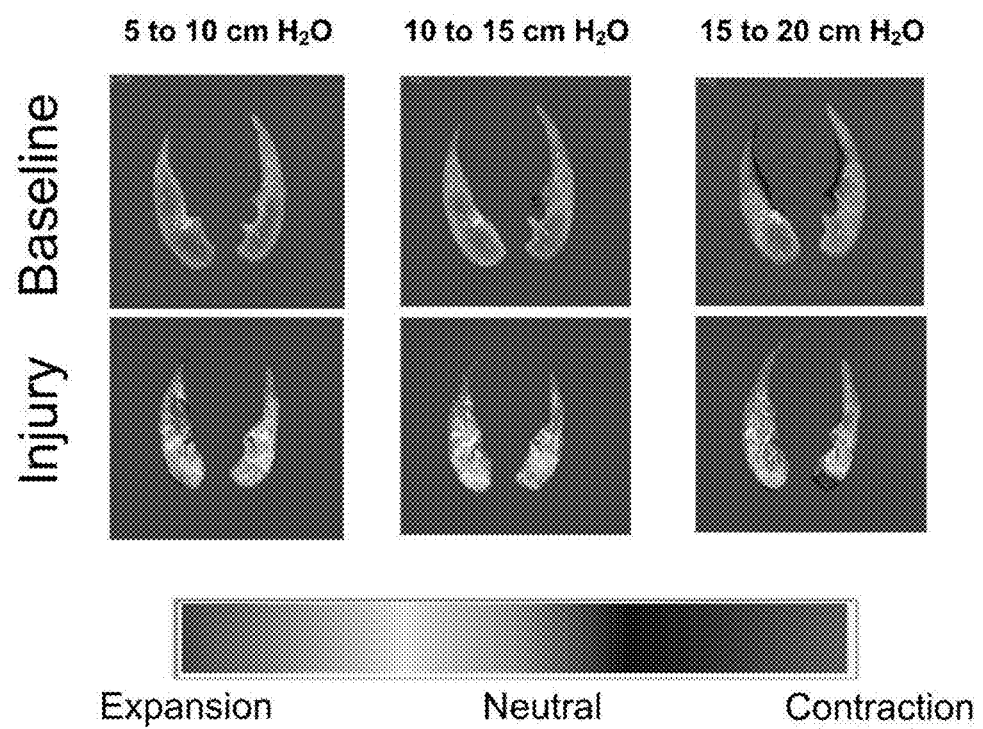
FIG. 8 illustrates CT images of lung expansion and contraction before and after injury.
Figure 9:
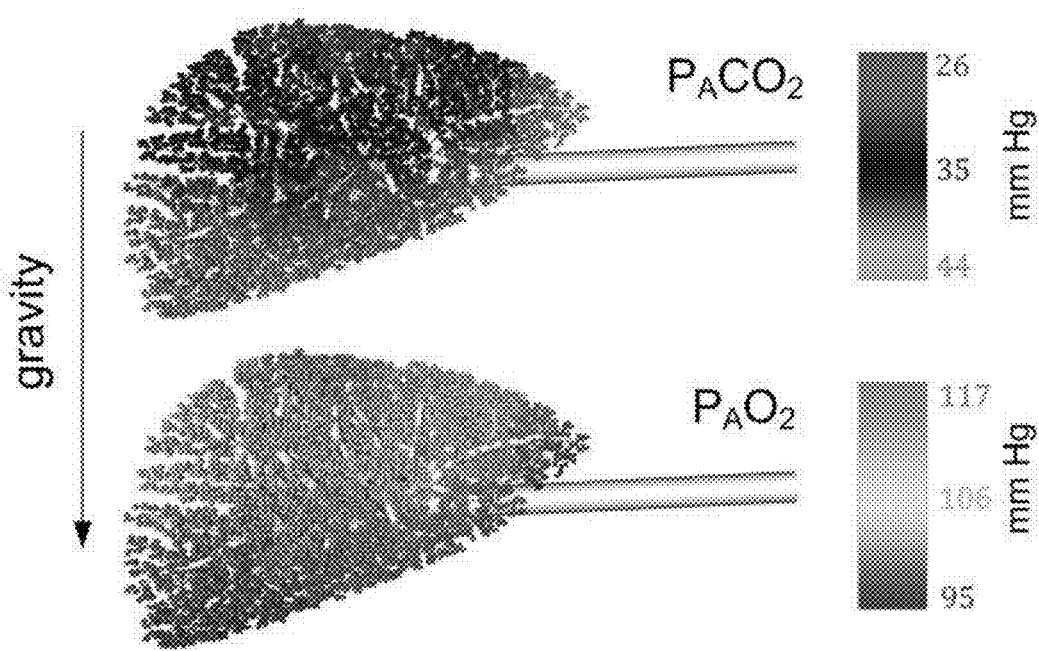
FIG. 9 illustrates anatomic distributions of acinar O2 and CO2 partial pressures of a lung in accordance with preferred embodiments of the invention.

Shown in FIGS. 8 and 9 are methods used to model the therapeutic treatment to be delivered to an individual patient 14. FIG. 8 illustrates regional lung expansion based on CT image registration in a canine lung before and after lung injury for 3 different inflation pressure ranges. This registered comparison between pre- and post-injury conditions shows the variation in regional expansion/contraction. Such regional variations are the result of the heterogeneity of the lung injury and the lung itself and clearly illustrate why the multi-frequency approach can help by synthesizing treatment regimens directed to different lung morphologies. FIG. 9 illustrates a simulation of the anatomic distributions of acinar $O_2$ and $CO_2$ partial pressures for a canine lung model ventilated with a $V_T$ of 10 cc $kg^{-1}$ at 20 breaths $min^{-1}$ using the gas exchange method. The granularity of the method (operating at the level of the acini) helps to better predict and target areas of different morphology using the MFOV technique.

To develop a mammalian model, thirteen preterm lambs (128 to 130 days gestation, term 150 days) weighing 3.15±0.39 kg were delivered via Cesarean section from anaesthetized ewes. Ewes had received 150 mg medroxyprogesterone intramuscularly at 100 days gestation, and 0.15 mg kg–1 betamethasone 72 and 48 hours prior to delivery. After delivery of the fetal head, the carotid and external jugular vessels were catheterized. Each lamb was intubated with a 4.5 mm cuffed endotracheal tube (ETT) via direct laryngoscopy. Lung liquid was manually aspirated using a 50 mL syringe. The fetal thorax was then exteriorized from the uterus and dried. In preparation for the EIT measurements, sixteen 23G needle electrodes were placed subcutaneously at equidistant locations around the chest ~3 cm above the xiphisternum. The electrodes were secured using a 5-cm-wide self-adherent bandage (Coban; 3M, St. Paul, Minn.). After cutting the umbilical cord, the lamb was weighed, placed prone in a radiant warmer, and given two recruitment maneuvers of 30 cmH2O of 10 second duration. The lamb was then stabilized for 30 minutes on CMV at a rate of 50 min–1, VT of 7 mL kg–1, PEEP of 6 cmH2O, and FiO2 of 30% (Fabian, ACUTRONIC Medical Systems AG, Switzerland). General anesthesia and suppression of spontaneous breathing efforts was maintained using continuous intravenous infusions of propofol (1 to 2 mg kg–1 min–1) and remifentanil (0.5 to 1.0 µg kg–1 min–1). Heart rate, arterial blood pressure, rectal temperature, and pre-ductal oxygen saturation (SpO2, as measured at the right ear) were monitored continuously (HP48S; Hewlett Packard, Andover, Mass.). Pressure (Pao) and flow ($\dot{V}$) were sampled at 200 Hz by the ventilator using a hot wire anemometer (Florian, Acutronics, Herzel, Switzerland) and pressure port at the proximal end of the endotracheal tube. Examples of instruments to measure pressure and flow include, but are not limited to, pressure transducers such as the PXLA75DN or PXLA02X5DN (Honeywell), Codman (Johnson & Johnson, Raynham, Mass.), 33NA002D (IC Sensors, Milpitas, Calif.), or LCVR-0002 (Celesco, Canoga Park, Calif.). In addition, a range of mesh- or screen-type heated pneumotachographs (e.g., Hans-Rudolph 3700) may be used. Volume delivered at the airway opening (V) was determined using trapezoidal integration of the sampled $\dot{V}$ signal.

Following the initial 30 minute period of CMV, each lamb was randomized to receive either SFOV or MFOV for 60 minutes, followed by a 30 minute CMV washout period and crossover to the alternative regimen for 60 minutes (FIG. 5). The SFOV waveform can consist of a pure sinusoidal volume waveform at 5 Hz (applied using a commercial Fabian system, ACUTRONIC AG), while the MFOV waveform can include a 5 Hz fundamental with additional energy at 10 Hz and 15 Hz (FIGS. 11A-11D). The MFOV waveform may be generated by modifications of the Fabian firmware to apply the method described herein. In accordance with various embodiments, the CMV, SFOV, or MFOV waveforms may be generated by a variety of ventilators, oscillators, and flow interrupters including, but not limited to, the Humming V or Novalung (Metran, Saitama, Japan), Sensormedics (Sensormedics, Yorba Linda, Calif.), STEPHAN HF (F. Stephan Medizintechnik, Gackenbach, Germany), Infant Star (Infrasonics, San Diego, Calif.), Babylog (Draegerwerk, Lubeck, Germany), Dufour (Valleneuve d'Aseq, France), or any other device that is or may be modified to become suitable to produce ventilator waveforms of the type described herein. These devices may generate the air flow with a proportional solenoid valve 17 or a piston solenoid. Peak-to-peak volume excursions (Vpp) were determined for both SFOV and MFOV as the difference between the maximum and minimum of the volume signal. After subtraction of the non-zero mean of the volume signal ($\overline{V}$), the root mean square of the discretized volume ($V_{rms}$) was determined as:

$$V_{rms} = \sqrt{\frac{1}{N}\sum_{n=1}^{N}(V_n - \overline{V})^2} \qquad (1)$$

where $V_n$ denotes the discretized volume waveform and N is the number of data points per each 0.2 second period of the SFOV or MFOV waveform. Dynamic respiratory system elastance ($E_{dyn}$) at 5 Hz was computed from 2 minute samples of $P_{ao}$ and $\dot{V}$ waveforms at 15 minute intervals during SFOV and MFOV, using a periodogram technique with a 1-second rectangular window and 80% overlap.

Figure 12:
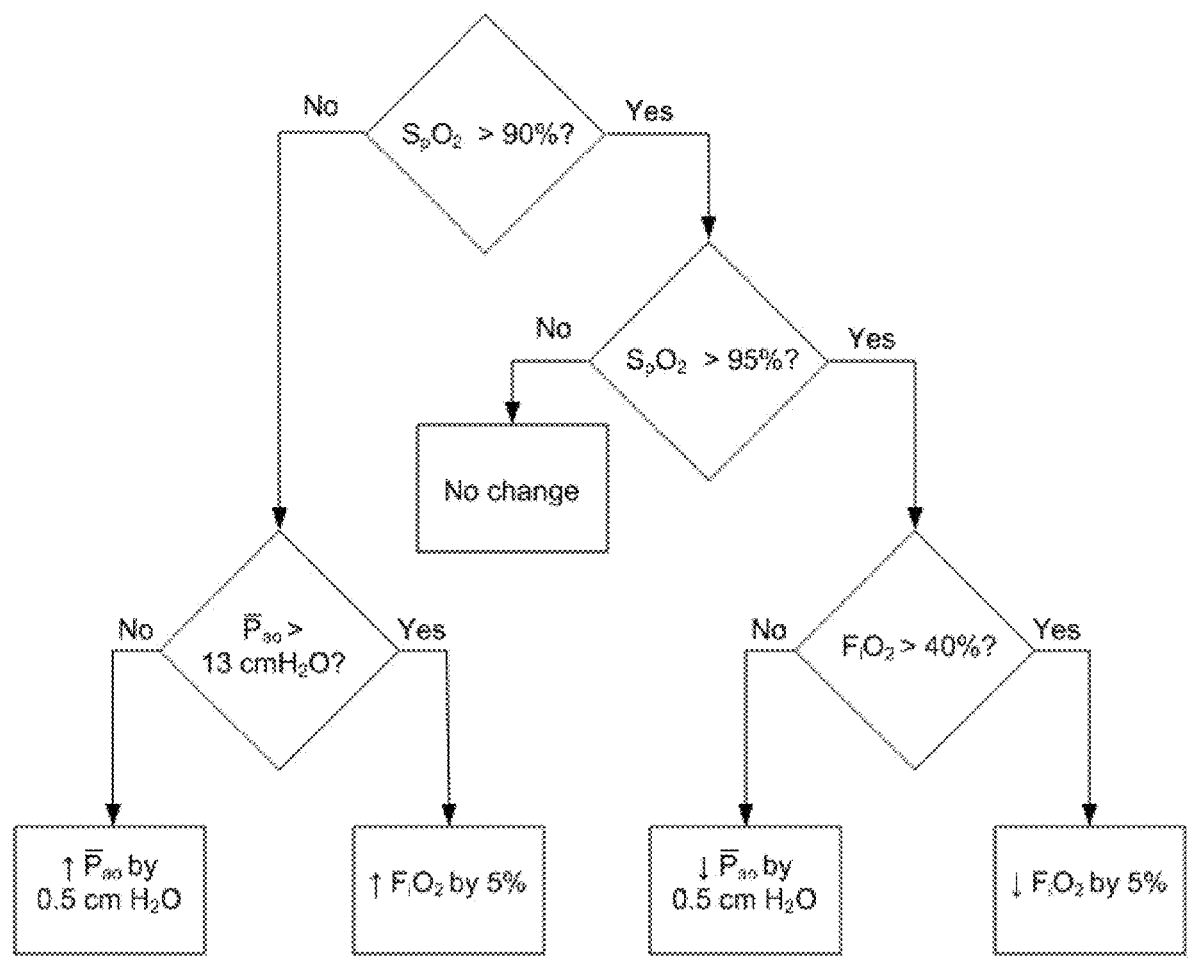
FIG. 12 illustrates a method for adjusting mean airway pressure ($\bar{P}_{ao}$) and fraction of inspired oxygen concentration ($FiO_2$) based on arterial oxygen saturation ($SpO_2$)
Figures 13A, 13B, 13C:
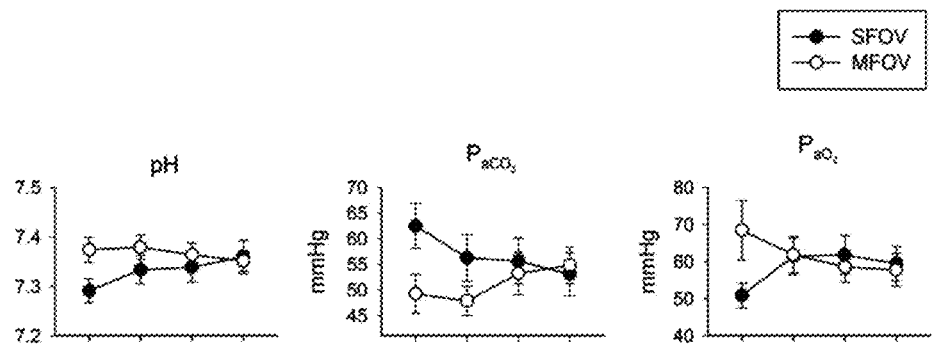
FIGS. 13A-13I illustrate (A) arterial pH, (B) arterial $CO_2$ tension ($P_aCO_2$) (C) arterial $O_2$ tension ($P_aO_2$), (D) peak-to-peak tidal volume normalized by weight, (VppWt−1), (E) root mean square volume normalized by weight (VmsWt−1), (F) ventilatory cost function (Vc), (G) mean airway pressure ($\bar{P}_{ao}$), (H) oxygenation index (OI), and (I) dynamic respiratory system elastance (Edyn) versus time during single-frequency oscillatory ventilation (SFOV, closed symbols) and multi-frequency oscillatory ventilation (MFOV, open symbols). An asterisk (*) indicates significant difference between SFOV and MFOV modalities, using two-way repeated measures ANOVA with Tukey HSD criterion. All data are expressed as mean+S.E.
Figures 13D, 13E, 13F:
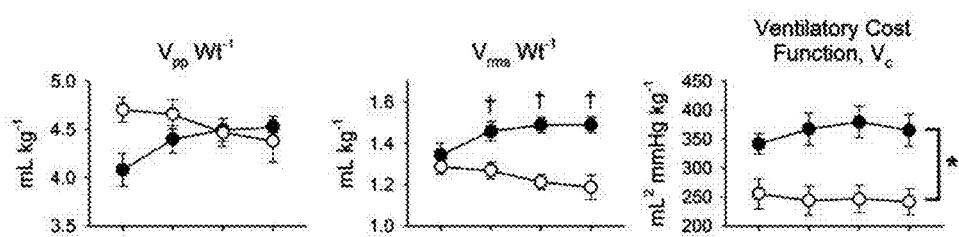
Figures 13G, 13H, 13I:
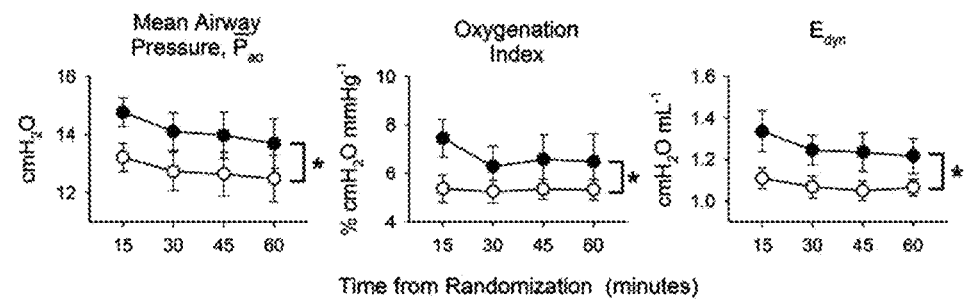

Arterial pH, carbon dioxide tension ($P_aCO_2$), and oxygen tension ($P_aO_2$) were obtained every 15 minutes throughout the entire protocol. During SFOV and MFOV, mean airway pressure ($\overline{P}_{ao}$) and % inspired $O_2$ fraction ($F_iO_2$) were adjusted as needed according to the method shown in FIG. 12. The oxygenation index (OI) was calculated as:

$$OI = \frac{F_iO_2 \overline{P}_{ao}}{P_aO_2} \qquad (2)$$

The $V_{rms}$ was increased or decreased by 0.01 mL $kg^{-1}$ at 15 minute intervals, for every 1 mmHg above or below our target $P_aCO_2$ range of 45 to 55 mmHg. Since $CO_2$ elimination during HFOV is roughly proportional to $V_T^2$, we defined a ventilatory cost function ($V_C$) to compare the efficiency of gas exchange for SFOV and MFOV:

$$V_C = (V_{rms}^2 P_a CO_2) Wt^{-1} \quad (3)$$

where Wt denotes body weight in kg. Thus for a given value of $P_a CO_2$, lower values of $V_C$ indicate more efficient ventilation. The results are illustrated in FIGS. 13A-13I.

Electrical Impedance Tomographic (EIT) measurements (FIG. 14) were analyzed at the end of each 60 minute SFOV and MFOV period (i.e., at t=90 and 180 minutes of the protocol) for both crossover groups, using the GOE-MF II system with Thorascan software (CareFusion, Höchberg, Germany). The EIT data were acquired at a resolution of 32×32 pixels and a frame rate of 44 Hz. The EIT images were reconstructed using the GREIT image reconstruction algorithm with anatomic boundary shapes based on a transverse CT-scan of the chest of a lamb at the same height. Further details regarding this image reconstruction algorithm are present in Adler, et al., "GREIT, a unified approach to 2D linear EIT reconstruction of lung images," Physiological Measurement 30 (2009) 535-555, the contents of which are hereby incorporated by reference herein. Thirty seconds of artifact-free representative data were chosen for analysis. To minimize cardiogenic disturbances, the EIT data was filtered using a 5th order digital Butterworth high-pass filter with 2 Hz cut-off frequency. From these filtered images, functional EIT (fEIT) images of ventilation were generated from the standard deviation of the time course of the impedance value within each pixel. From the fEIT images, the spatial distribution of ventilation within each of the 32 equally sized right-to-left and anterior-to-posterior slices could be determined. The geometric center of ventilation within each 32×32 fEIT image was computed using the technique of Frerichs et al. (Frerichs et al., "Monitoring perioperative changes in distribution of pulmonary ventilation by functional electrical impedance tomography", Acta Anaesthesiol Scand 1998; 42: 721-726, the contents of which are hereby incorporated by reference herein).

Birth weights and umbilical cord blood gas values at delivery were compared between the two groups of lambs using two-tailed Student's t-tests. Group A were randomized to receive SFOV first followed by MFOV, while Group B first received MFOV followed by SFOV. At the end of the initial and washout 30 minute CMV periods, gas exchange and mechanics data for the two groups were compared using a two-way analysis of variance (ANOVA), with group (A vs. B) and period (initial vs. washout) as variable components. During the 60 minute SFOV and MFOV periods, gas exchange and mechanics data were analyzed via two-way repeated measures ANOVA, with treatment mode (SFOV vs. MFOV) and time (in 15 minute increments) as the variable components. EIT ventilation distributions were analyzed via three-way ANOVA, with treatment mode, group, and hemithorax (left vs. right) as the variable components. If significance was obtained with ANOVA, post hoc comparisons were performed using the Tukey HSD criterion. Unless otherwise specified, all data are expressed as mean±S.D., and $P<0.05$ was considered statistically significant.

Of the thirteen lambs, seven were randomized to receive SFOV first followed by MFOV (Group A), and six were randomized to receive MFOV first followed by SFOV (Group B). There were no significant differences in birth weights or umbilical cord pH, PaCO2, and PaO2 values between the two groups (Table 1).

TABLE 1

Birth weights and umbilical cord blood gas data for the thirteen lambs at time of delivery, separated into Groups A and B. Data are expressed as mean ± S.D. Significance assessed by t-test with the exception of pH, which was assessed by Wilcoxon Rank Sum Test.

|  | Group A (n = 7) | Group B (n = 6) | Significance |
| --- | --- | --- | --- |
| Wt (kg) | 3.18 ± 0.41 | 3.11 ± 0.39 | 0.77 |
| pH | 7.33 ± 0.06 | 7.33 ± 0.20 | 0.39 |
| $P_a CO_2$ (mm Hg) | 57.0 ± 3.7 | 61.6 ± 6.2 | 0.15 |
| $P_a O_2$ (mm Hg) | 31.9 ± 2.6 | 27.7 ± 8.9 | 0.29 |

Wt: weight; pH: negative base 10 logarithm of the hydrogen ion concentration; $P_a CO_2$: arterial partial pressure of carbon dioxide; $P_a O_2$: arterial partial pressure of oxygen.

FIGS. 13A-13I summarize the gas exchange and mechanics data at 15 minute intervals for the SFOV and MFOV modalities. No significant differences were observed in arterial pH at any time point between the two modalities, although the PaCO2 was significantly higher for SFOV at 15 minutes compared to MFOV. However, normalized Vpp was significantly lower for SFOV compared to MFOV for the first 15 minutes after randomization. Normalized Vrms was significantly higher for SFOV compared to MFOV for all time points after 15 minutes. Finally VC, mPao, OI, and Edyn were significantly lower at all time points during MFOV compared to SFOV.

Figure 14:
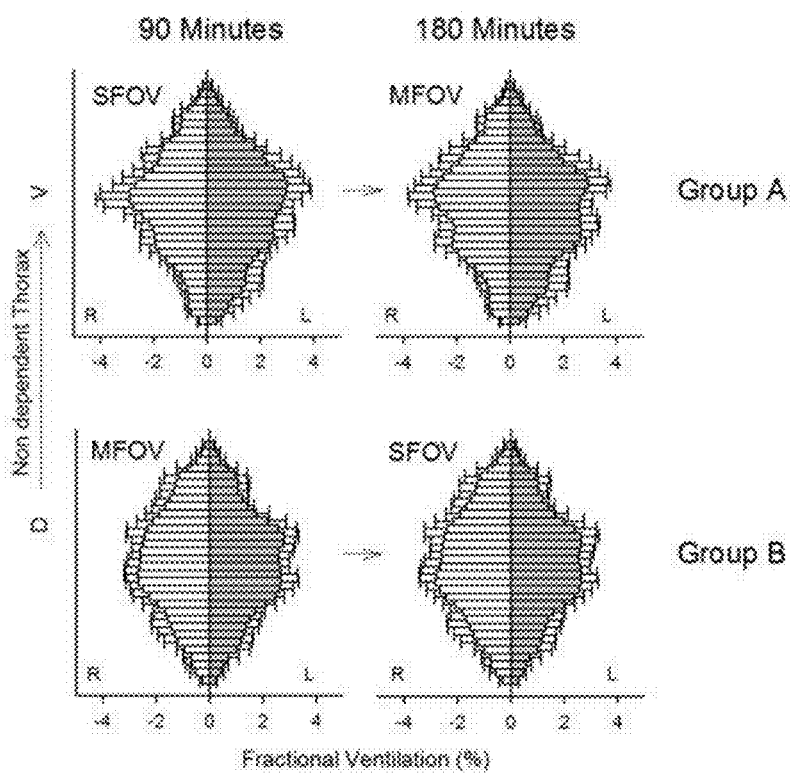
FIG. 14 shows fractional distribution of ventilation within 32 slices of the left (gray bars) and right (white bars) hemithoraces following one hour of SFOV and MFOV modalities (i.e., at 90 and 180 minutes of the protocol) for Groups A (n=6) and B (n=6). Direction from dependent to nondependent slices is indicated by vertical arrow; Data are expressed as mean+S.D. of functional EIT values; Anatomic directions are denoted as R: right; L: left; V; ventral; D: dorsal.
Figure 15A:
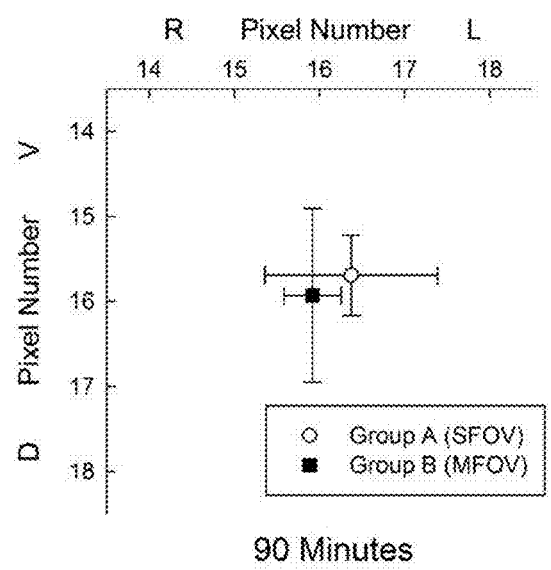
FIGS. 15A-15B illustrate geometric centers of ventilation within the fEIT images (32×32 pixels) following one hour of SFOV and MFOV modalities (i.e., at 90 and 180 minutes of the protocol) for Groups A (n=6) and B (n=6); Pixels are referenced relative to the upper left original for each panel; Anatomic directions are denoted as R: right; L: left; V: ventral; D: dorsal; Data are expressed as mean+S.D. of the geometric centers of ventilation
Figure 15B:
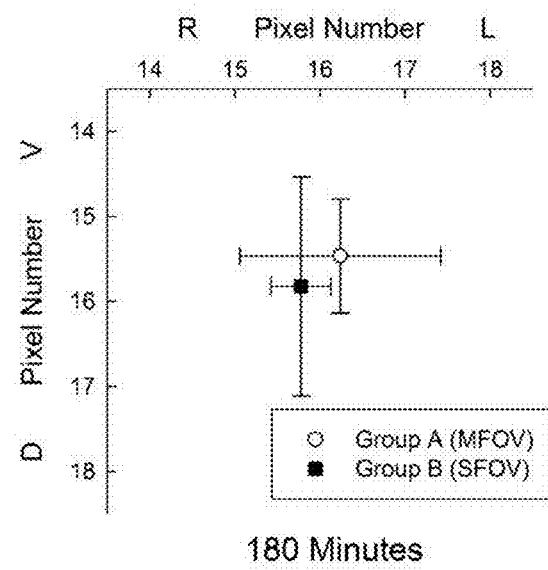

FIG. 14 shows the spatial distribution of ventilation at the end of each 60 minute SFOV or MFOV period (i.e., at 90 and 180 minutes of the protocol) for Groups A and B. Due to an electrode failure, one lamb from Group A was omitted from the EIT analysis. No significant differences were observed in ventilation distribution between the oscillatory modalities (SFOV vs. MFOV), groups (A vs. B), or right vs left and anterior vs posterior hemithoraces. There was also no significant difference in the geometric center of ventilation between the two groups (FIGS. 15A and 15B).

Premature lungs exhibit mechanical and spatial heterogeneity due to structural immaturity and surfactant deficiency. Conventional mechanical ventilation (CMV) in preterm infants may inadvertently worsen existing lung injury due to repeated alveolar overdistention and opening/closing of airways. By contrast, high frequency oscillatory ventilation (HFOV) achieves effective gas exchange with relatively high mean airway pressures to sustain lung recruitment, with small tidal volumes to prevent end-inspiratory overdistention. However, numerous clinical trials in adults and neonates with ARDS have shown that HFOV does not reduce mortality, despite physiological evidence of enhanced gas distribution, volume recruitment, and $\dot{V}/\dot{Q}$ matching. Why such a theoretically promising mode of mechanical ventilation has so far failed to prove advantageous in clinical practice may be multifactorial: oscillation strategy, treatment end points, and/or operator skills are potential contributing factors. The failure of HFOV suggests suboptimal aeration and ventilation of the injured lung, potentially arising from variable regional effects of frequency, amplitude, and mean airway pressure in the setting of heterogeneous disease processes. There is no doubt that the mechanical complexity of the heterogeneous lung is fundamental to the distribution of ventilation.

Figure 2:
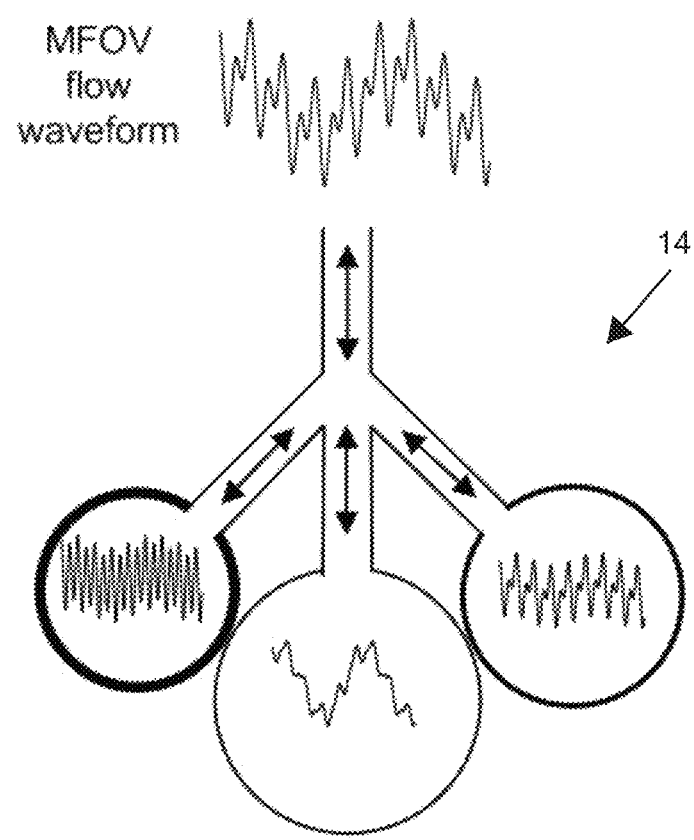
FIG. 2 schematically illustrates selective delivery of different frequency components to different regions of the lung in accordance with preferred embodiments of the invention.

As shown in FIG. 2, lung function and gas exchange would improve if volume oscillations are applied at multiple frequencies simultaneously, rather than at a single high frequency. Multiple frequencies improve oxygenation and $\dot{V}/\dot{Q}$ matching by distributing ventilation more evenly to different regions, according to their respective local mechanical properties. Multi-frequency oscillatory ventilation (MFOV) using a hybrid ventilator-oscillator results in a more uniform distribution of ventilation to the alveoli compared to traditional SFOV. The mechanism for such improved functional outcomes is optimization of regional gas distribution, due to inclusion of frequencies that are more appropriate for the local mechanical properties of the heterogeneous parenchyma.

Figures 10A, 10B, 10C:
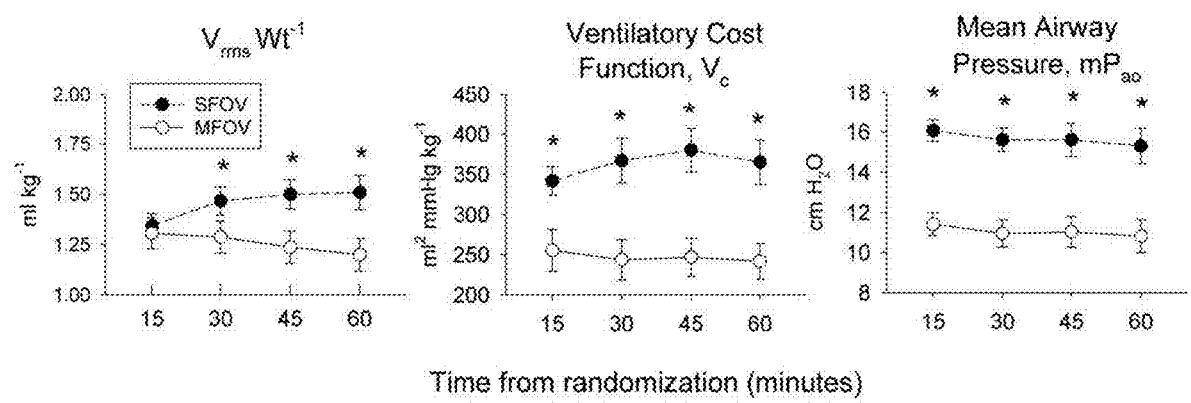
FIGS. 10A-10C graphically illustrate root mean square of delivered volume, ventilatory cost function, and mean airway pressure, respectively.
Figure 11A:
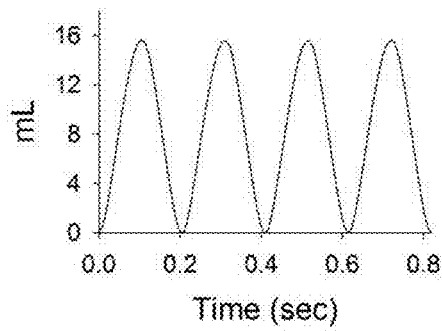
FIGS. 11A-11D show representative examples of time-domain tracings (left panels A and C) and magnitude spectra (right panels B and D) for SFOV and MFOV volume waveforms, as generated by an oscillator in accordance with the invention.
Figure 11B:
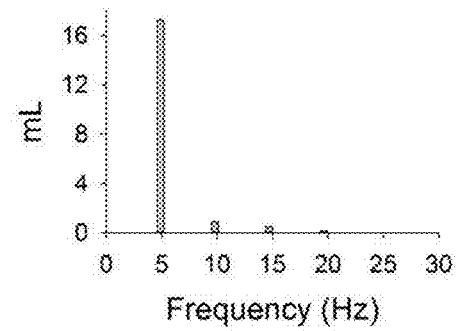
Figure 11C:
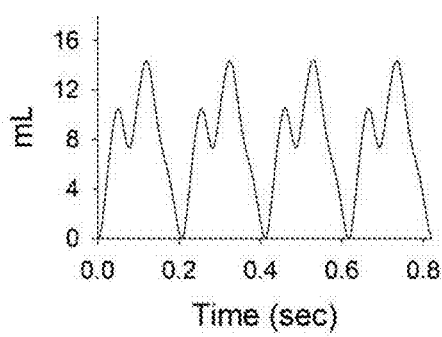
Figure 11D:
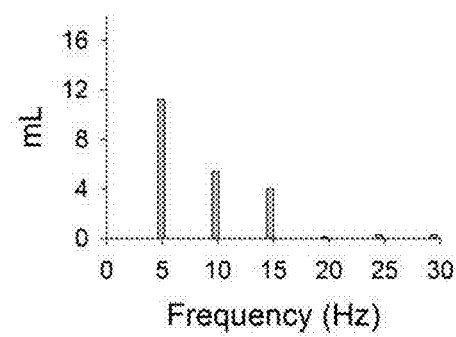

To assess the efficacy of MFOV, certain indices of gas exchange and mechanics may be evaluated. The ventilatory cost function ($V_C$) is defined as the product of ventilatory 'power' ($V_{rms}^2$) multiplied by arterial $CO_2$ tension ($P_aCO_2$). This index is justified by empiric evidence that CO2 elimination is roughly proportional to the square of tidal volume during HFOV. Our $V_C$ index was significantly lower during MFOV compared to SFOV, consistent with more efficient $CO_2$ elimination (FIG. 10B). More efficient $CO_2$ elimination in MFOV was due largely to the increased $V_{rms}$ required of the SFOV modality compared to MFOV in order to maintain $P_aCO_2$ within our desired target range of 45 to 55 mm Hg: there were no significant differences in the peak-to-peak volume excursions or $P_aCO_2$ between SFOV and MFOV after 15 minutes (FIG. 10A).

The OI and $\bar{P}_{ao}$ were significantly lower at all time points during MFOV compared to SFOV, with no significant differences in $P_aO_2$. These findings indicate that MFOV facilitates more efficient oxygenation at lower distending pressures. The $E_{dyn}$ was also significantly reduced during MFOV, although we cannot be certain whether lower $E_{dyn}$ was the result of enhanced lung recruitment or reduced parenchymal strain-stiffening. The lower $E_{dyn}$ further suggests that the enhanced spectral content of the MFOV waveforms may prevent time-dependent derecruitment of lung units, as the higher frequency components may act as a dithering mechanism to keep lung units opened.

The mechanism for improved gas exchange and global mechanics during MFOV provides improvement of regional gas distribution, due to the presence of additional frequencies that are more appropriate for the local mechanical properties of the heterogeneous parenchyma. The primary determinant of ventilation distribution in the injured lung is the distribution of regional mechanical properties of the airways and parenchyma, such as resistance, inertance, and elastance. Local ventilation distribution becomes highly frequency-dependent in the presence of regional mechanical heterogeneity. Thus, the most effective frequency for optimal gas exchange can vary from region to region. Oscillation at a single high frequency (i.e., standard HFOV) results in large portions of a heterogeneous lung being simultaneously underventilated and overventilated, with corresponding decrements in gas exchange and worsening injury. Previous methods using computational models indicate that small amplitude volume oscillation at a single, arbitrary frequency is not suitable for reaching the majority of the gas exchanging regions in spatially heterogeneous lung. Thus MFOV is better suited to complement the heterogeneous mechanics of the immature lung, by allowing the local impedances of the injured parenchyma to selectively filter out flows of 'less-desirable' frequencies. As a result, flows at frequencies more optimal for a particular region pass through and participate in gas exchange.

Despite the improved metrics of gas exchange and mechanics with MFOV, the ventilation distribution as assessed with EIT did not demonstrate significant differences between the SFOV and MFOV modalities. However, EIT provides a low-resolution assessment of ventilation distribution based on changes in electrical impedance, and only within a single cross-sectional slice of the thorax. Despite its utility as a potential bedside tool for rapid, noninvasive quantification of regional aeration, EIT may not describe ventilation distribution appropriately during HFOV modalities due to its 16-electrode array and maximum sampling rate of 44 Hz. Alternative methods for assessing the spatial distribution of ventilation, such dynamic volumetric computed tomography during Xenon washout, can be used for the high temporal variations associated with MFOV.

Certain commercially-available oscillators generate waveforms with higher harmonics above the fundamental frequency, although there is no evidence to suggest that these harmonic frequency artifacts influence clinical efficacy. This disclosure, on the other hand, is directed to the efficacy found from the use of multiple specifically tuned frequencies or broadband waveform patterns.

While these measurements are compelling, they are limited by: 1) a small sample size; 2) a MFOV waveform consisting of only three frequencies that were not optimized for the heterogeneous lung; and 3) minimal information on the mechanical properties of these preterm lungs. Despite these deficiencies, the data indicate that MFOV has distinct advantages as a ventilator modality in preterm lungs compared to traditional HFOV, and maintains lung recruitment at lower mean airway pressures. A larger sample size in an animal model more representative of heterogeneous clinical ARDS would further strengthen the concept of MFOV, and establish its use in eventual human clinical trials.

Mechanical heterogeneity in the injured lung has important implications for optimal treatment strategies in ARDS. This oscillatory modality improves gas exchange, specifically with regard to convective ventilation. With adjustments in oscillatory pressure amplitude and mean airway pressure, MFOV can improve gas exchange while minimizing the detrimental effects of cyclic alveolar overdistention and derecruitment.

MFOV provides in improved gas exchange at lower distending pressures in an animal model of preterm lung injury. MFOV has far-reaching implications for both pulmonary medicine and anesthesia. For example, MFOV is not limited to being a treatment solely for pediatric or adult ARDS, but is useful in the ventilator management of other diseases that affect the lungs in a heterogeneous manner such as asthma, COPD, or pneumonia. Moreover, MFOV can more efficiently penetrate 'difficult-to-reach' regions of the lung has implications for the optimal delivery of aerosols and drugs, such as beta agonists, steroids, or even inhaled volatile anesthetics.

MFOV is a more efficient ventilatory modality in preterm lungs compared to SFOV, and maintains lung recruitment at lower mean airway pressures. The spectral content of MFOV waveforms can be enhanced to improve gas exchange and result in less injurious ventilation compared to more conventional ventilation and oscillation strategies. MFOV can significantly change the care of critically-ill, ventilated patients.

While preferred embodiments and implementations of the invention have been set forth for purposes of illustration, the foregoing description should not be deemed a limitation of the invention disclosed herein. Accordingly, various modifications, adaptations and alternatives may occur to one skilled in the art without departing from the spirit and the scope of the present invention.

What is claimed is:

1. A system comprising:
an oscillatory ventilator configured for oscillating at a plurality of specifically tuned sinusoidal frequencies simultaneously a ventilation gas for delivery to a lung region of a patient; and
a ventilator control system, in communication with the oscillatory ventilator, to control a sinusoidal waveform input for the oscillatory ventilator, wherein the sinusoidal waveform input comprises the plurality of specifically tuned sinusoidal frequencies each of which sinusoidal frequencies are below the acoustic range.

2. The system of claim 1, wherein the sinusoidal waveform input further comprises of an amplitude and phase associated with each of the plurality of sinusoidal frequencies, wherein the amplitude and phase for each of the plurality of sinusoidal frequencies is independently configurable.

3. The system of claim 2, wherein one of the amplitude and phase associated with each of the plurality of sinusoidal frequencies is alterable in response to physical or physiologic changes in the patient.

4. The system of claim 1, wherein the ventilator control system further comprises, at least two signal generators wherein each signal generator produces a signal comprising of a specifically tuned sinusoidal frequency, amplitude, and phase that are combined to produce the sinusoidal waveform input.

5. The system of claim 1, wherein information about a status of a patient's respiratory system is used to determine the plurality of specifically tuned sinusoidal frequencies applied during a therapeutic treatment period.

6. The system of claim 1, wherein the ventilator control system provides a first plurality of specifically tuned sinusoidal frequencies and a second plurality of specifically tuned sinusoidal frequencies that are different than the first plurality of specifically tuned sinusoidal frequencies during a therapeutic period.

7. The system of claim 1, wherein the plurality of specifically tuned sinusoidal frequencies are determined and applied independently of each other, and wherein the plurality of specifically tuned sinusoidal frequencies are each fundamental frequencies.

8. The system of claim 1, and further comprising at least one sensor for measuring the ventilation gas being delivered to the lung region of the patient and providing the measurement to the ventilator control system for use in producing the sinusoidal waveform input.

9. The system of claim 8, wherein the ventilator control system further comprises an input device for receiving a measurement from the at least one sensor and for receiving at least one measurement corresponding to physiological characteristics of the patient, wherein the physiological characteristics include at least one chosen from, airway flow, mechanical impedance, ventilation-to-perfusion ratio, ventilation distribution, arterial pH, arterial tension of carbon dioxide, or arterial tension of oxygen,
a computer in communication with the input device for processing information from the input device, and an output device in communication with the computer for controlling the operating parameters of the oscillatory ventilator, including the frequency, amplitude, and phase characteristics of the applied sinusoidal waveform input.

10. The system of claim 1, wherein the oscillatory ventilator further comprises a proportional solenoid valve for translating the waveform input from the ventilation control system to a ventilation gas waveform that corresponds to the sinusoidal waveform input.

11. A method comprising:
producing a sinusoidal waveform input comprising a plurality of specifically tuned sinusoidal frequencies, each of which sinusoidal frequencies are below the acoustic range; and oscillating a volume of gas with an oscillatory ventilator for delivery to a lung region of a patient based on the sinusoidal waveform input.

12. The method of claim 11, wherein the plurality of specifically tuned sinusoidal frequencies of the sinusoidal waveform input comprise a frequency, an amplitude, and a phase.

13. The method of claim 11, wherein the sinusoidal waveform comprises of a plurality of specifically tuned sinusoidal frequencies, with each of the plurality of specifically tuned sinusoidal frequencies further comprising an amplitude, phase, and power.

14. The method of claim 13, wherein the sinusoidal waveform further comprises a plurality of specifically tuned sinusoidal frequencies applied simultaneously to the oscillatory ventilator.

15. The method of claim 11, and further comprising treating the patient with one or more alternating periods of conventional ventilation, single frequency oscillatory ventilation, and multi-frequency oscillatory ventilation comprising oscillating with the oscillatory ventilator gas for delivery to the lung region of the patient based on the sinusoidal waveform input.

16. The method of claim 11, and further comprising tuning a plurality of sinusoidal frequencies based on physiological characteristics of the patient during a therapeutic treatment period.

17. The method of claim 16, wherein the physiological characteristics include at least one chosen from airway pressure, airway flow, mechanical impedance, delivered concentration of gas species, ventilation-to-perfusion ratio, ventilation distribution, arterial pH, arterial tension of carbon dioxide, and arterial tension of oxygen.

18. A method of treating a patient, the method comprising:
producing a sinusoidal waveform input comprising a plurality of specifically tuned sinusoidal frequencies below the acoustic range;
oscillating a volume of gas with an oscillatory ventilator for delivery to a lung region of the patient based on the sinusoidal waveform input; and
evaluating a status of the patient.

19. The method of claim 18, and further comprising modifying at least one of the plurality of specifically tuned sinusoidal frequencies of the sinusoidal waveform input in order to modify a sinusoidal waveform of the ventilation gas for delivery to the patient.

20. The method of claim 19, wherein modifying the at least one of the plurality of specifically tuned sinusoidal frequencies of the sinusoidal waveform further comprises at least one chosen from a frequency, an amplitude, and a phase of the sinusoidal waveform.

* * * * *